US007790386B2

(12) United States Patent
Ku et al.

(10) Patent No.: US 7,790,386 B2
(45) Date of Patent: Sep. 7, 2010

(54) NEISSERIA GONORRHOEAE SPECIFIC OLIGONUCLEOTIDE SEQUENCES

(75) Inventors: Lailing Ku, Pleasanton, CA (US); Charlene Bush-Donovan, Livermore, CA (US); David Sherman, Davis, CA (US); Qi Meng, Fremont, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 311 days.

(21) Appl. No.: 11/784,502

(22) Filed: Apr. 6, 2007

(65) Prior Publication Data

US 2008/0090240 A1 Apr. 17, 2008

Related U.S. Application Data

(60) Provisional application No. 60/790,197, filed on Apr. 7, 2006.

(51) Int. Cl.
*C12Q 1/68* (2006.01)
*C12P 19/34* (2006.01)
*C07H 21/04* (2006.01)

(52) U.S. Cl. ................. 435/6; 435/91.2; 536/24.32; 536/24.33

(58) Field of Classification Search ............ 435/6, 435/91.2; 536/24.32, 24.33
See application file for complete search history.

(56) References Cited

U.S. PATENT DOCUMENTS

| 5,210,015 | A | 5/1993 | Gelfand et al. ............ 435/6 |
|---|---|---|---|
| 5,256,536 | A | 10/1993 | Miyada et al. ............ 435/6 |
| 5,487,792 | A | 1/1996 | King et al. ............ 136/256 |
| 5,525,717 | A | 6/1996 | Miyada et al. ......... 536/24.32 |
| 5,550,040 | A | 8/1996 | Purohit et al. |
| 5,804,375 | A | 9/1998 | Gelfand et al. ............ 435/6 |
| 5,962,273 | A | 10/1999 | Durmowicz et al. ....... 435/91.1 |
| 5,976,805 | A | 11/1999 | You et al. ............ 435/6 |
| 6,090,557 | A | 7/2000 | Weiss et al. |
| 6,214,979 | B1 | 4/2001 | Gelfand et al. ......... 536/22.1 |

FOREIGN PATENT DOCUMENTS

| EP | 0 630 971 | 12/1994 |
|---|---|---|
| EP | 0317077 | 1/1996 |
| EP | 0915173 | 5/1999 |
| EP | 0919633 | 8/2002 |
| EP | 1586663 | 10/2005 |
| JP | 2005 278443 | 10/2005 |
| WO | WO/01/86001 | 11/2001 |

OTHER PUBLICATIONS

Lowe et al., Nucleic Acids Research 18(7), 1757-1761 (1990).*
Buck et al., Design Strategies and Performance of Custom DNA Sequencing Primers, BioTechniques, 27:3, pp. 528-536 (1999).
Database Genbank, Carrick et al, *Neisseria gonorrhoeae* complete cds of rsp, orf250, pivNG genes, toposomerase subunit ParC gene, partial cds, (2001).
European Search Report, P42834EP/KVC, filed on Nov. 31, 2007.
Miyada, et al., *Molecular and Cellular Probes*, 5:327-335, 1991.
Chaudry, et al., *Current Science*, 83:634-640, 2002.
Carrick et al., "*Neisseria gonorrhaeae* contains multiple copies of a gene that may encode a specific recombinase and is associated with DNA rearrangements", *Gene*, 1998, 220: 21-29.
Dempsey et al., "Physical map of the chromosome of *Neisseria gonorrhoeae* FA1090 with locations of genetic markers, including opa and pil genes", *J. Bacteriol.*, 1991, 173: 5476-5486.
Dempsey and Cannon, "Locations of genetic markers on the physical map of the chromosome of *Neisseria gonorrhoeae* FA1090", *J. Bacteriol.*, 1994, 176: 2055-2060.
Miyada and Born, "A DNA sequence for the discrimination of *Neisseria gonorrhoeae* from other *Neisseria* species", *Mol. Cell. Probes*, 1991, 5: 327-335.
Skaar et al., "Analysis of the Piv recombinase-related gene family of *Neisseria gonorrhoeae*", *J. Bacteriol.*, 2005, 187: 1276-1286.

* cited by examiner

*Primary Examiner*—Kenneth R. Horlick
(74) *Attorney, Agent, or Firm*—Karla Weyand

(57) ABSTRACT

The present invention relates to oligonucleotide sequences for amplification primers and detection probes and their use in nucleic acid amplification methods for the selective and specific detection of *Neisseria gonorrhoeae* in biological samples. The invention also provides oligonucleotide primer sets and primer/probe sets in the form of kits for the detection and diagnosis of gonococcal infection. The inventive oligonucleotide primers and probes can also be used in combination with other specific oligonucleotide primers and probe for the simultaneous detection of *Neisseria gonorrhoeae* and other target organisms, such as *Chlamydia trachomatis*.

29 Claims, 5 Drawing Sheets

| SEQ ID NO. | Sequence Name* | Map Location | Sequence (5' → 3') | Strand |
|---|---|---|---|---|
| 1 | NG1-ORF1-251-FP | 251-271 | GCGGATTCCCTTGTCAAGATT | (+) |
| 2 | NG1-ORF1-315-RP | 299-315 | GCCGCGCTCACCCTCTA | (−) |
| 3 | NG1-ORF1-273-"c" probe | 273-296 | R-TTCCATGATTTGGAAACAGCCGGG-Q | (+) |
| 4 | NG1-ORF1-273-"r.c." probe | 273-296 | R-CCCGGCTGTTTCCAAATCATGGAA-Q | (−) |
| 5 | NG2-ORF1-531-FP | 531-557 | AGTACGTTTGGATACAGGATTTGATTT | (+) |
| 6 | NG2-ORF1-601-RP | 583-601 | AGCCGTTTTCGCCAGTTTC | (−) |
| 7 | NG2-ORF1-561-"c" probe | 561-581 | R-CCATCCGAACCGACGCACAA-Q | (+) |
| 8 | NG3-ORF1-800-FP | 800-820 | GGAACGAGCCATCAAAAACAA | (+) |
| 9 | NG3-ORF1-870-RP | 850-870 | GCGGTTCAGGGAAGTGATAGC | (−) |
| 10 | NG3-ORF1-824-"c" probe | 824-847 | R-TTGCAGCAGGTGGCGGTGGTACTT-Q | (+) |
| 11 | NG3-ORF1-824-"r.c." probe | 824-847 | R-AAGTACCACCGCCACCTGCTGCAA-Q | (−) |
| 12 | NG4-ORF1-764-FP | 764-788 | AAGGTATGATTAGCCACGTTATCG | (+) |
| 13 | NG4-ORF1-838-RP | 819-838 | CGCCACCTGCTGCAATAAT | (−) |
| 14 | NG4-ORF1-790-"c" probe | 790-815 | R-CGTATGCATCGGAACGAGCCATCAAA-Q | (+) |
| 15 | NG5-pivNG-113-FP | 3583-3603 | GCCTTTTTCCTTTCGGGATT | (+) |
| 16 | NG5-pivNG-183-RP | 3629-3653 | GTACATAAGAAAGGCGGAGATTACG | (−) |
| 17 | NG5-pivNG-135-"c"probe | 3605-3627 | R-ACGCCGATTTGTAACGCGATGGA-Q | (+) |
| 18 | NG5-pivNG-135-"r.c." probe | 3605-3627 | R-TCCATCGCGTTACAAATCGGCGT-Q | (−) |
| 19 | NG6-pivNG-510-FP | 3980-3998 | GACGCTTCACGCCTTCCTT | (+) |
| 20 | NG6-pivNG-593-RP | 4040-4063 | CCATGAATGAACAGCTTGAAGTTT | (−) |
| 21 | NG6-pivNG-535-"c"probe | 4005-4037 | R-AGGCTTCTCCGTCTGTCTTTTATCTCTCCTT-Q | (+) |
| 22 | NG7-pivNG-794-FP | 4264-4285 | GCATCCTGTTTGTCTGTTTGG | (+) |
| 23 | NG7-pivNG-871-RP | 4317-4341 | TTACGTAGTGAATCCGCTGAAAATA | (−) |
| 24 | NG7-pivNG-818-"c"probe | 4288-4315 | R-CGCTTGAACCTGCTTTCTGCATACTTGC-Q | (+) |
| 25 | NG8-pivNG-1017-FP | 4487-4504 | CCGAATGCTCCGTTTGC | (+) |
| 26 | NG8-pivNG-1091-RP | 4537-4561 | GTAACGCCGTAGGATTGGATATATC | (−) |
| 27 | NG8-pivNG-1038-"c"probe | 4508-4532 | R-CCATGGCGGATGCGTTAAAGGTCAG-Q | (+) |
| 28 | NG8-pivNG-1038-"r.c."probe | 4508-4532 | R-CTGACCTTTAACGCATCCGCCATGG-Q | (−) |

Table 1 (Part 1 of 2)

Table 1 (Part 2 of 2)

| SEQ ID NO. | Sequence Name* | Map Location | Sequence (5' → 3') | Strand |
|---|---|---|---|---|
| 29 | NG9-pivNG-983-FP | 4453-4478 | TGATCTAAACCTTTGAATCGTTGTC | (+) |
| 30 | NG9-pivNG-1053-RP | 4507-4523 | AACGCATCCGCCATGGT | (-) |
| 31 | NG9-pivNG-1010-"c"probe | 4480-4504 | R-AACTTTGCCGAATGCTCCGTTTTGC-Q | (+) |
| 32 | NG6-pivNG-510 FP | 3980-3998 | GACGCTTCACGCCTTCCTT | (+) |
| 33 | NG6-pivNG-593 RP | 4040-4063 | CCATGAATGAACAGCTTGAAGTTT | (-) |
| 34 | NG6-pivNG-535 probe | 4005-4023 | R-AGGCTTCTCCGTCTGCTCT-Q | (+) |
| 35 | NG6 FP02 pivNG -484FP | 3954-3974 | TCTGCCTATTGCCGGTATGGT | (+) |
| 36 | NG6 RP05 pivNG -717 | 4167-4187 | GAAGCGGCCAAAGCATATGC | (-) |
| 37 | NG6-pivNG-535 probe | 4005-4023 | R-AGGCTTCTCCGTCTGCTCT-Q | (+) |
| 38 | NG6 FP01 pivNG -492FP | 3962-3981 | ATTGCCGTATGGTTTCAA | (+) |
| 39 | NG6 RP05 pivNG -717 | 4167-4187 | GAAGCGGCCAAAGCATATGC | (-) |
| 40 | NG6-pivNG-535 probe | 4005-4023 | R-AGGCTTCTCCGTCTGCTCT-Q | (+) |
| 41 | NG6 FP03 pivNG -479FP | 3949-3970 | GTCATTCTGCCTATTGCCGGT | (+) |
| 42 | NG6 RP05 pivNG -717 | 4167-4187 | GAAGCGGCCAAAGCATATGC | (-) |
| 43 | NG6-pivNG-535 probe | 4005-4023 | R-TGCATCCAATCAGATTTCCTTTCG-Q | (+) |
| 44 | NG6 FP02 pivNG -484FP | 3954-3974 | TCTGCCTATTGCCGGTATGGT | (+) |
| 45 | NG6 RP05 pivNG -717 | 4167-4187 | GAAGCGGCCAAAGCATATGC | (-) |
| 46 | NG6 pivNG-513 probe | 3983-4003 | R-GCTTCACGCCTTCCTTGCAGTTA-Q | (+) |
| 47 | NG6 FP02 pivNG -484FP | 3954-3974 | TCTGCCTATTGCCGGTATGGT | (+) |
| 48 | NG6 RP05 pivNG -632 | 4167-4187 | GAAGCGGCCAAAGCATATGC | (-) |
| 49 | NG6 pivNG-516 probe | 3986-4003 | R-TCACGCCTTCCTTGCAGTTA-Q | (+) |
| 50 | NG9-pivNG-983 FP | 4453-4478 | TGATCTAAACCTTTGAATCGTTGTC | (+) |
| 51 | NG8-pivNG-1091 RP | 4537-4561 | GTAACGCCGTAGGATTGGATATATC | (-) |
| 52 | NG8-pivNG-1038 probe | 4508-4532 | R-CCATGGCGGATGCGTTAAAGGTCAG-Q | (+) |

* "c" stands for complementary to the coding or sense strand (+), and "r.c." stands for reverse complementary to the coding or sense strand (-).

| Prime-Probe Set # | NG1 | NG2 | NG3 | NG4 | NG5 | NG6 | NG7 | NG8 | NG9 |
|---|---|---|---|---|---|---|---|---|---|
| $10^4$ DNA copies of NG | + | + | + | + | + | + | + | + | + |
| $10^4$ DNA copies of CT | - | - | - | - | - | - | - | - | - |

Table 2

| ID | Organisms | ID | Organisms |
|---|---|---|---|
| 1 | Acinetobacter calcoaceticus | 38 | N. lactamica |
| 2 | Bacteroides thetaiotaomicron | 39 | N. lactamica |
| 3 | Candida albicans | 40 | N. lactamica |
| 4 | Candida glabrata | 41 | N. lactamica |
| 5 | Chlamydia pneumoniae | 42 | N. lactamica |
| 6 | Chlamydia psittaci | 43 | N. meningitidis A |
| 7 | Citrobacter freundi | 44 | N. meningitidis A |
| 8 | Corynebacterium renale | 45 | N. meningitidis B |
| 9 | E.coli | 46 | N. meningitidis C |
| 10 | Enterobacter aerogenes | 47 | N. meningitidis C |
| 11 | Garnerella vaginalis | 48 | N. meningitidis C |
| 12 | Streptococcus pyogenes (Group A beta) | 49 | N. meningitidis D |
| 13 | Streptococcus agalactiae (Group B beta) | 50 | N. meningitidis X |
| 14 | Haemophilus influenzae | 51 | N. meningitidis Y |
| 15 | Helicobacter pylori | 52 | N. meningitidis Z |
| 16 | Herpes simplex virus I | 53 | N. mucosa |
| 17 | Herpes simplex virus II | 54 | N. mucosa |
| 18 | Kingella kingae (as Moraxella kingae) | 55 | N. mucosa var. heidelbergenesis |
| 19 | Klebsiella oxytoca | 56 | N. perflava |
| 20 | Klebsiella pneumoniae | 57 | N. perflava |
| 21 | Lactobacillus brevis | 58 | N. perflava |
| 22 | Lactobacillus delbrueckii subsp lactis | 59 | N. perflava |
| 23 | Moraxella catarrhalis | 60 | N. polysacchareae |
| 24 | Moraxella Branhamella catarrhalis | 61 | N. sicca |
| 25 | Moraxella lacunata | 62 | N. sicca |
| 26 | Moraxella osloensis | 63 | N. sicca |
| 27 | Mycoplasma hominis | 64 | N. subflava |
| 28 | N. cinerea | 65 | N. subflava |
| 29 | N. elongata | 66 | Proteus mirabilis |
| 30 | N. elongata subsp.glycolytica | 67 | Ruminococcus productus (as Pepetostreptococcus) |
| 31 | N. elongata subsp.nitroreducens | 68 | Salmonella minnesota |
| 32 | N. elongata subsp.nitroreducens | 69 | Salmonella typhimurium |
| 33 | N. flava | 70 | Staphylococcus agalactiae |
| 34 | N. flavescens | 71 | Staphylococcus aureus |
| 35 | N. flavescens | 72 | Trichomonas vaginalis |
| 36 | N. flavescens | 73 | Ureaplasma urealyticum |
| 37 | N. flavescens | 74 | Vibrio Cholerae |

Table 3

| CT/GC Multiplex Assay | CT | GC |
|---|---|---|
| *Chlamydia Trachomatis* at 10 IFU/mL (A, B, Ba, C, D, E, F, G, H, I, J, K, L1, L2 and L3) | + | N/A |
| *Neisseria gonorrhea* at 50 copies/rxn (IA 1-22, IB 1-32) | N/A | + |

Table 4

NEISSERIA GONORRHOEAE SPECIFIC OLIGONUCLEOTIDE SEQUENCES

RELATED APPLICATIONS

This application claims priority from Provisional Application U.S. Ser. No. 60/790,197 filed on Apr. 7, 2006 and entitled "*Neisseria Gonorrhoeae* Specific Oligonucleotide Sequences". The provisional application is incorporated herein by reference in its entirety.

BACKGROUND OF THE INVENTION

Gonorrhea is a sexually transmitted disease (STD) caused by the human pathogen, *Neisseria gonorrhoeae* (gonococcus), a Gram-negative, intracellular, aerobic *diplococcus* that can grow and rapidly multiply in the mucous membranes. Gonococcal infection remains a major global health problem with more than sixty million cases reported annually worldwide (A. C. Gerbase et al., Lancet, 1998, 351 (Suppl. 3): 2-4). According to the Centers for Disease Control and Prevention (CDC), gonorrhea is the second most frequently reported STD in the United States with almost 400,000 new cases reported each year (CDC, "*Summary of Notifiable Disease—United States. 2001*", Morb. Mortal. Wkly Rep., 2001, 50:1-108; CDC, "*Sexually Transmitted Disease Surveillance, 2001*", U.S. Department of Health and Human Services, Atlanta, Ga., 2002; CDC, "*Sexually Transmitted Disease Surveillance, 2002*", U.S. Department of Health and Human Services, Atlanta, Ga., 2003). Like chlamydia, the most prevalent bacterial STD in the U.S., gonorrhea is substantially under-reported, and approximately twice as many new infections are estimated to occur each year as are reported (H. Weinstock et al., Persp. Sex. Reprod. Health, 2004, 36: 6-10). Under-reporting is substantial, at least in part, because gonorrhea is asymptomatic in 30-60% of infected women and up to 10% of infected men. Unrecognized and untreated, *Neisseria gonorrhoeae* may remain infectious in the host for several months, which may facilitate its spread and promote a reservoir of infection.

When they are present, initial symptoms of gonococcal infection in women include dysuria, vaginal discharge, vaginal bleeding between periods, and abdominal pain. Left untreated, women with gonorrhea are at risk of developing serious complications from the infection, regardless of the presence or severity of symptoms. In particular, gonorrhea can lead to a severe, painful pelvic infection with inflammation of the fallopian tubes and ovaries called pelvic inflammatory disease (PID) (E. W. Hook III and H. H. Handsfield, in "*Sexually Transmitted Diseases*", K. K. Holmes et al. (Eds.), 3$^{rd}$ Ed., 1999, pp. 451-466, McGraw-Hill: New York, N.Y.). PID can cause permanent damage to the fallopian tubes, uterus, and surrounding tissues, which can lead to chronic pelvic pain, infertility, and potentially fatal ectopic pregnancy (W. Cates Jr. et al., Am. J. Obstet. Gynecol., 1991, 164: 1771-1781; J. Coste et al., Fertil. Steril., 1994, 62: 289-295; L. Weström and P. Wolner-Hansen, Genitourin. Med., 1993, 69: 9-17). In men, the most common initial symptoms are dysuria and purulent discharge from the urethra. The average incubation for gonorrhea is approximately 2 to 5 days following sexual contact with an infected partner; however, symptoms may appear as late as 30 days. *Neisseria gonorrhoeae* may spread from the urethra to other portions of the male reproductive tract causing epididymitis, prostatitis, and various other conditions such as periurethral abscess. Untreated gonorrhea may lead to urethral stricture, which can result in decreased urine flow, incomplete emptying of the bladder, urinary tract infection, and ultimately kidney failure. Rarely (in 1-3% of infected women and a lower percentage of infected men), the bacterium disseminates via the blood causing arthritis, bacteremia or endocarditis (E. W. Hook III and H. H. Handsfield, in "*Sexually Transmitted Diseases*", K. K. Holmes et al. (Eds.), 3$^{rd}$ Ed., 1999, pp. 451-466, McGraw-Hill: New York, N.Y.). Although gonorrhea is known primarily as a sexually transmitted infection, it can also be transmitted to the newborn during delivery through an infected birth canal. This can cause blindness, joint infection or a life-threatening blood infection to the baby.

Although patients with any sexually transmitted disease are at increased risk of co-infection with another STD, co-infection of chlamydia and gonorrhea is most common (up to 40% of women and up to 20% of men with gonorrhea are also infected with chlamydia). Epidemiologic and biologic studies provide strong evidence that gonococcal infections increase susceptibility to and facilitate transmission of human immunodeficiency virus (HIV) in both men and women (M. S. Cohen et al., Lancet, 1997, 349: 1868-1873; D. T. Fleming and J. N. Wasserheit, Sex. Transm. Infect., 1999, 75: 3-17; K. A. Workowski and W. C. Levine, Morb. Mortal. Wkly Rep., 2002, 51 (RR06): 1-80; T. A. Farley et al., J. Acquir. Immun. Defic. Syndr., 2003, 33: 642-648).

Early detection is an essential component of public health programs to control gonococcal infection. The goals of early detection and early treatment include interruption of the chain of transmission, prevention of long-term sequelae, and reduction of duration of infectiousness to limit the risk of co-infection. Early detection may also prevent over-treatment, which is a major concern due to widespread *N. gonorrhoeae* antibiotic resistance (CDC, "*Fluoroquinolone-resistance in Neisseria gonorrhoeae, Hawaii, 1999, and decreased susceptibility to azithromycin in N. gonorrhoeae, Missouri, 1999*", Morb. Mortal. Wkly Rep., 2000, 49: 833-837; CDC, "*Increases in fluoroquinolone-resistant Neisseria gonorrhoeae—Hawaii and California, 2001*", Morb. Mortal. Wkly Rep., 2002, 51: 1041-1044; CDC, "*Increases in fluoroquinolone-resistant Neisseria gonorrhoeae among men who have sex with men—United States, 2003, and revised recommendations for gonorrhea treatment, 2004*", Morb. Mortal. Wkly Rep., 2004, 53: 335-338).

Isolation of *Neisseria gonorrhoeae* in cell culture has been the traditional method for laboratory diagnosis and has remained the method of choice for medico-legal specimens because of its specificity. However, this method requires stringent transport conditions to preserve specimen viability and has a turnaround time of 2 to 3 days. In many settings, cell culture has been replaced by more rapid tests based on antigen detection by direct fluorescent antibody staining, enzyme immunoassays, and enzyme-linked immunosorbent assays (ELISA), which have less demanding transport requirements and can provide results on the same day. However, these methods are still laborious and time-consuming and, more importantly, lack sensitivity as screening assays, especially for asymptomatic patients.

More recently, nucleic acid-based hybridization probe tests have been developed for direct detection of *Neisseria gonorrhoeae*. These tests offer higher specificity but no substantial improvement on sensitivity. Furthermore, most of these tests are performed on endocervical or urethral specimens, which are obtained using invasive sampling procedures. Nucleic acid amplification assays based on polymerase chain reaction (PCR), ligase chain reaction (LCR), strand-displacement amplification (SDA), or transcription-mediated amplification (TMA) technology are now available. In addition to offering all the advantages of non-culture tests in terms of ambient specimen transport, batching automation, and rapid processing time, these assays provide higher specificity and a sensitivity approaching 100%. Furthermore, they can be performed on less invasive clinical specimens such as urine. All these advantages make nucleic acid amplification assays particularly suited for detection of asymptomatic gonococcal infection and as a screening tool.

However, existing nucleic acid amplification assays for gonorrhea detection still exhibit certain disadvantages and limitations. The primary concerns involve false-negative results caused by the presence of amplification inhibitors in certain specimens and false-positive results due to cross-contamination if strict quality control procedures are not applied. Clearly, the development of improved nucleic acid amplification assays for the detection of gonococcal infection remains highly desirable.

SUMMARY OF THE INVENTION

The present invention is directed to systems and methods for the rapid, selective and specific detection of *Neisseria gonorrhoeae* in biological samples. In particular, the invention encompasses reagents that can be used for developing nucleic acid amplification tests for the detection and diagnosis of gonococcal infection. More specifically, the invention provides oligonucleotide sequences that can be used as amplification primers and/or detection probes for the detection of either strand of target nucleic acid sequences within the open reading frame-1 (ORF1) gene, the cytosine methyltransferase (dcmG) gene and the pilin inverting protein homolog (pivNG) gene of *Neisseria gonorrhoeae*.

More specifically, the present invention provides isolated oligonucleotides comprising a nucleic acid sequence selected from the group consisting of SEQ ID Nos. 1-52 (see Table 1), any active fragments thereof, and any combinations thereof.

In certain embodiments, the inventive oligonucleotide sequences are provided as primer sets or primer/probe sets that can be used in any of a variety of nucleic acid amplification assays including those involving real-time and/or multiplex detection.

The present invention also provides methods for detecting *Neisseria gonorrhoeae* in a biological test sample. Generally, such methods comprise contacting a test sample suspected of containing a *Neisseria gonorrhoeae* nucleic acid with at least one inventive oligonucleotide such that the oligonucleotide can hybridize to the *Neisseria gonorrhoeae* nucleic acid, if present in the sample; and detecting any oligonucleotide hybridized to the *Neisseria gonorrhoeae* nucleic acid. Detection of hybridization of the oligonucleotide to the *Neisseria gonorrhoeae* nucleic acid indicates the presence of *Neisseria gonorrhoeae* in the sample.

Other methods of the present invention comprise contacting a test sample suspected of containing a *Neisseria gonorrhoeae* nucleic acid with at least one primer set or primer/probe set described herein and amplification reaction reagents to form a reaction mixture. The reaction mixture is then placed under amplification conditions so as to amplify all or a portion of the *Neisseria gonorrhoeae* nucleic acid, if present in the test sample, using primers of the primer set or primer/probe set to generate *Neisseria gonorrhoeae* amplicons. The resulting *Neisseria gonorrhoeae* amplicons may be detected using any of a variety of detection technologies. In certain embodiments, a hybrid is formed between a *Neisseria gonorrhoeae* amplicon and a detection probe of the primer/probe set and detected as an indication of the presence of *Neisseria gonorrhoeae* in the test sample.

The inventive oligonucleotide sequences can be used in combination with other specific primers and probes in a nucleic acid amplification format for the simultaneous detection of *Neisseria gonorrhoeae* and other target organisms. In certain embodiments, the amplification primers and detection probes of the present invention are used in combination with *Chlamydia trachomatis* specific primers and probes for the simultaneous detection of *Neisseria gonorrhoeae* and *Chlamydia trachomatis* in biological samples.

The present invention also provides kits comprising amplification primers, detection probes, primer sets or primer/probe sets, as disclosed herein and, optionally, amplification reaction reagents.

These and other objects, advantages and features of the present invention will become apparent to those of ordinary skill in the art having read the following detailed description.

BRIEF DESCRIPTION OF THE DRAWING

Table 1 (parts 1 and 2) shows examples of inventive specific oligonucleotide sequences derived from the open reading frame-1 (ORF1) gene, cytosine methyltransferase (dcmG) gene and pilin inverting protein homolog (pivNG) gene sequences of *Neisseria gonorrhoeae*. The map positions and SEQ. ID No. of each oligonucleotide are indicated in the table.

Table 2 shows the results of a single-plex TaqMan kPCR assay using nine sets of amplification primers and detection probes described in Table 1. All the primer/probe sets were found to be efficient at detecting *Neisseria gonorrhoeae* (GC), and showed no cross-reaction with *Chlamydia trachomatis* (CT) target DNA.

Table 3 is a list of 74 organisms closely related to *Neisseria gonorrhoeae*, that were used to test the cross-reactivity of some primer/probe sets of the invention.

Table 4 shows the results of a multiplex TaqMan kPCR assay which was used to test fifteen (15) different *Chlamydia trachomatis* (CT) serovars and forty-six (46) different *Neisseria gonorrhoeae* (GC) isolates.

DEFINITIONS

Throughout the specification, several terms are employed that are defined in the following paragraphs.

The terms "individual", "subject" and "patient" are used herein interchangeably. They refer to a human being that can be the host of *Neisseria gonorrhoeae*, but may or may not be infected by the bacterium. The terms do not denote a particular age, and thus encompass adults, children, newborns, as well as fetuses.

The term "test sample", as used herein, refers to any liquid or solid material suspected of containing *Neisseria gonorrhoeae* nucleic acids. A test sample may be, or may be derived from, any biological tissue or fluid that can contain *Neisseria gonorrhoeae* nucleic acids. Frequently, the sample will be a "clinical sample", i.e., a sample obtained or isolated from a patient to be tested for gonococcal infection. Such samples include, but are not limited to, bodily fluids which contain cellular materials and may or may not contain cells, e.g., blood, plasma, serum, urine, seminal fluid, saliva, ocular lens fluid, lymphatic fluid, amniotic fluid, and the like; endocervical, urethral, rectal, vaginal, vulva-vaginal, nasopharyngeal and pulmonary samples; and archival samples with known diagnosis. Test samples may also be sections of tissues such as frozen sections. The term "test sample" also encompasses any material derived by processing a biological sample.

Derived materials include, but are not limited to, cells (or their progeny) isolated from the sample, cell components, and nucleic acid molecules extracted from the sample. Processing of biological samples to obtain a test sample may involve one or more of: filtration, distillation, centrifugation, extraction, concentration, dilution, purification, inactivation of interfering components, addition of reagents, and the like.

The terms "nucleic acid", "nucleic acid molecule" and "polynucleotide" are used herein interchangeably. They refer to a deoxyribonucleotide or ribonucleotide polymer in either single-stranded or double-stranded form, and unless otherwise stated, encompass known analogs of natural nucleotides that can function in a similar manner as naturally occurring nucleotides. The terms encompass nucleic acid-like structures with synthetic backbones, as well as amplification products.

The term "oligonucleotide", as used herein, refers to a short string of deoxyribonucleotide or ribonucleotide polymer. Oligonucleotides can be used as amplification primers and/or detection probes. Such short stretches of nucleic acid sequences are often chemically synthesized. As will be appreciated by those skilled in the art, the length of an oligonucleotide (i.e., the number of nucleotides that it contains) can vary widely, often depending on its intended function or use. Generally, oligonucleotides comprise between about 5 and about 150 nucleotides, preferably between about 15 and about 100 nucleotides, more preferably between about 15 and about 50 nucleotides.

The term "isolated" when referring to an oligonucleotide means an oligonucleotide, which by virtue of its origin or manipulation, is separated from at least some of the components with which it is naturally associated or with which it is associated when initially obtained or prepared. By "isolated", it is alternatively or additionally meant that the oligonucleotide of interest is produced or synthesized by the hand of man.

The term "active fragment", as used herein in reference to an oligonucleotide (e.g., an oligonucleotide sequence provided herein), refers to any nucleic acid molecule comprising a nucleotide sequence sufficiently homologous to or derived from the nucleotide sequence of the oligonucleotide, which includes fewer nucleotides than the full length oligonucleotide, and retains at least one biological property of the entire sequence. Typically, active fragments comprise a sequence with at least one activity of the full length oligonucleotide. An active fragment or portion of an oligonucleotide sequence of the present invention can be a nucleic acid molecule which is, for example, 10, 15, 20, 25, 30 or more nucleotides in length and can be used as amplification primer and/or detection probe for the detection of *Neisseria gonorrhoeae* in a biological sample.

The term "sufficiently homologous", when used herein in reference to an active fragment of an oligonucleotide, refers to a nucleic acid molecule that has a sequence homology of at least 35% compared to the oligonucleotide. In certain embodiments, the sequence homology is at least 40%, at least 60%, at least 80%, at least 90%, at least 95%, or more.

The terms "homology" and "identity" are used herein interchangeably, and refer to the sequence similarity between two nucleic acid molecules. Calculations of the percent homology or identity of two nucleic acid sequences, can be performed by aligning the two sequences for optimal comparison purposes (e.g., gaps can be introduced in one or both of a first and a second nucleic acid sequence for optimal alignment and non-homologous sequences can be disregarded for comparison purposes). In certain embodiments, the length of a sequence aligned for comparison purposes is at least 30%, at least 40%, at least 60%, at least 80%, at least 90%, at least 95% or 100% of the length of the reference sequence. The nucleosides at corresponding nucleotide positions are then compared. When a position in the first sequence is occupied by the same nucleotide as the corresponding position in the second sequence, then the molecules are identical (or homologous) at that position. The percent identity between the two sequences is a function of the number of identical positions shared by the sequences, taking into account the number of gaps, and the length of each gap, which needs to be introduced for optimal alignment of the two sequences.

The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0), using a PAM120 weight residue table, a gap length penalty of 12 and a gap penalty of 4. The percent identity between two nucleotide sequences can, alternatively, be determined using the GAP program in the GCG software package (available at http://www.gcg.com), using a NWSgapdna.CMP matrix.

The term "hybridization" refers to the formation of complexes between nucleotide sequences which are sufficiently complementary to form complexes via Watson-Crick base pairing or non-canonical base pairing. When a primer "hybridizes" with a target sequence (template), such complexes (or hybrids) are sufficiently stable to serve the priming function required by, e.g., the DNA polymerase, to initiate DNA synthesis. It will be appreciated that hybridizing sequences need not have perfect complementarity to provide stable hybrids. In many situations, stable hybrids will form where fewer than about 10% of the bases are mismatches. Accordingly, as used herein, the term "complementary" refers to an oligonucleotide that forms a stable duplex with its complement under assay conditions, generally where there is about 90% or greater homology. Those skilled in the art understand how to estimate and adjust the stringency of hybridization conditions such that sequences having at least a desired level of complementarity will stably hybridize, while those having lower complementarity will not. For examples of hybridization conditions and parameters see, e.g., J. Sambrook et al., "*Molecular Cloning: A Laboratory Manual*", 1989, Second Edition, Cold Spring Harbor Press: Plainview, N.Y.; F. M. Ausubel, "*Current Protocols in Molecular Biology*", 1994, John Wiley & Sons: Secaucus, N.J.

As used herein, the term "amplification" refers to a method or process that increases the representation of a population of specific nucleic acid sequences in a sample. Amplification methods (such as polymerase chain reaction or PCR) are known in the art and are discussed in more detail below.

The terms "target sequence" and "target nucleic acid" are used herein interchangeably. They refer to a nucleic acid sequence, the presence or absence of which is desired to be detected. In the context of the present invention, a target sequence preferably includes a nucleic acid sequence to which oligonucleotide primers will complex. The target sequence may also include a probe-hybridizing region with which a probe will form a stable hybrid under desired conditions. As will be recognized by one of ordinary skill in the art, a target sequence may be single-stranded or double-stranded. In the context of the present invention, target sequences of interest are located within the open reading frame-1 (ORF1)

gene, the cytosine methyltransferase (dcmG) gene or the pilin inverting protein homolog (pivNG) gene of *Neisseria gonorrhoeae*.

The terms "primer" and "amplification primer" are used herein interchangeably. they refer to an oligonucleotide which is capable of acting as a point of initiation of synthesis of a primer extension product that is a complementary strand of DNA, when placed under suitable conditions (e.g., buffer, salt, temperature and pH) in the presence of nucleotides and an agent for nucleic acid polymerization (e.g., a DNA-dependent or RNA-dependent polymerase). The primer is preferably single-stranded for maximum efficiency in amplification, but may alternatively be double-stranded. If double-stranded, the primer may first be treated (e.g., denatured) to allow separation of its strands before being used to prepare extension products. Such a denaturation step is typically performed using heat, but may alternatively be carried out using alkali, followed by neutralization. A typical primer contains about 10 to about 35 nucleotides in length of a sequence substantially complementary to the target sequence. However, a primer can also contain additional sequences. For example, amplification primers used in Strand Displacement Amplification (SDA) preferably include a restriction endonuclease recognition at site 5' to the target binding sequence (see, for example, U.S. Pat. Nos. 5,270,184 and 5,455,166). Nucleic Acid Sequence Based Amplification (NASBA), and Transcription-Mediated Amplification (TMA) primers preferably include an RNA polymerase promoter linked to the target binding sequence of the primer. Methods for linking such specialized sequences to a binding target sequence for use in a selected amplification reaction are well-known in the art.

The terms "forward primer" and "forward amplification primer" are used herein interchangeably, and refer to a primer that hybridizes (or anneals) with the target (template strand). The terms "reverse primer" and "reverse amplification primer" are used herein interchangeably, and refer to a primer that hybridizes (or anneals) to the complementary target strand. The forward primer hybridizes with the target sequence 5' with respect to the reverse primer.

The term "amplification conditions", as used herein, refers to conditions that promote annealing and/or extension of primer sequences. Such conditions are well-known in the art and depend on the amplification method selected. Thus, for example, in a PCR reaction, amplification conditions generally comprise thermal cycling, i.e., cycling of the reaction mixture between two or more temperatures. In isothermal amplification reactions, amplification occurs without thermal cycling although an initial temperature increase may be required to initiate the reaction. Amplification conditions encompass all reaction conditions including, but not limited to, temperature and temperature cycling, buffer, salt, ionic strength, pH, and the like.

As used herein, the term "amplification reaction reagents", refers to reagents used in nucleic acid amplification reactions and may include, but are not limited to, buffers, reagents, enzymes having reverse transcriptase and/or polymerase activity or exonuclease activity; enzyme cofactors such as magnesium or manganese; salts; and deoxynucleotide triphosphates (dNTPs) such as deoxyadenosine triphosphate (dATP), deoxyguanosine triphosphate (dGTP), deoxycytidine triphosphate (dCTP), deoxythymidine triphosphate (dTTP) and deoxyuridine triphosphate (dUTP). Amplification reaction reagents may readily be selected by one skilled in the art depending on the amplification method used.

The terms "probe" and "detection probe" are used herein interchangeably and refer to an oligonucleotide capable of selectively hybridizing to at least a portion of a target sequence under appropriate conditions (e.g., a portion of a target sequence that has been amplified). In general, a probe sequence is identified as being either "complementary" (i.e., complementary to the coding or sense strand (+)), or "reverse complementary" (i.e., complementary to the anti-sense strand (−)). In certain embodiments, a detection probe is labeled with a detectable moiety.

The terms "labeled" and "labeled with a detectable agent (or moiety)" are used herein interchangeably to specify that an entity (e.g., an oligonucleotide detection probe) can be visualized, for example following binding to another entity (e.g., an amplification reaction product or amplicon). Preferably, the detectable agent or moiety is selected such that it generates a signal which can be measured and whose intensity is related to (e.g., proportional to) the amount of bound entity. A wide variety of systems for labelling and/or detecting nucleic acid molecules are well-known in the art. Labeled nucleic acids can be prepared by incorporation of, or conjugation to, a label that is directly or indirectly detectable by spectroscopic, photochemical, biochemical, immunochemical, electrical, optical, chemical or other means. Suitable detectable agents include, but are not limited to, radionuclides, fluorophores, chemiluminescent agents, microparticles, enzymes, colorimetric labels, magnetic labels, haptens, Molecular Beacons, and aptamer beacons.

The terms "fluorophore", "fluorescent moiety", and "fluorescent dye" are used herein interchangeably. They refer to a molecule that absorbs a quantum of electromagnetic radiation at one wavelength, and emits one or more photons at a different, typically longer, wavelength in response. Numerous fluorescent dyes of a wide variety of structures and characteristics are suitable for use in the practice of the invention. Methods and materials are known for fluorescently labeling nucleic acid molecules (see, for example, R. P. Haugland, "*Molecular Probes: Handbook of Fluorescent Probes and Research Chemicals 1992-1994*", 5$^{th}$ Ed., 1994, Molecular Probes, Inc.). Preferably, a fluorescent moiety absorbs and emits light with high efficiency (i.e., has a high molar absorption coefficient at the excitation wavelength used, and a high fluorescence quantum yield), and is photostable (i.e., does not undergo significant degradation upon light excitation within the time necessary to perform the analysis). Rather than being directly detectable themselves, some fluorescent dyes transfer energy to another fluorescent dye in a process called fluorescent resonance energy transfer (FRET), and the second dye produces the detected signal. Such FRET fluorescent dye pairs are also encompassed by the term "fluorescent moiety". The use of physically linked fluorescent reporter/quencher moiety is also within the scope of the present invention. In these embodiments, when the fluorescent reporter and quencher moiety are held in close proximity, such as at the ends of a nucleic acid probe, the quencher moiety prevents detection of a fluorescent signal from the reporter moiety. When the two moieties are physically separated, such as, for example, after cleavage by a DNA polymerase, the fluorescent signal from the reporter moiety becomes detectable.

The term "directly detectable", when used herein in reference to a label or detectable moiety, means that the label or detectable moiety does not require further reaction or manipulation to be detectable. For example, a fluorescent moiety is directly detectable by fluorescence spectroscopy methods. The term "indirectly detectable", when used herein in reference to a label or detectable moiety, means that the label or detectable moiety becomes detectable after further reaction or manipulation. For example, a hapten becomes detectable after reaction with an appropriate antibody attached to a reporter, such as a fluorescent dye.

DETAILED DESCRIPTION OF CERTAIN PREFERRED EMBODIMENTS

As mentioned above, the present invention relates to methods and reagents for detecting *Neisseria gonorrhoeae* in biological samples. In certain embodiments, the inventive methods use *Neisseria gonorrhoeae*-specific oligonucleotide sequences and sensitive nucleic acid amplification-based techniques that allow detection of *Neisseria gonorrhoeae* in samples containing even small amounts of the bacterium cells.

I—Oligonucleotide Sequences for Amplification Primers and Detection Probes

Inventive Oligonucleotide Sequences

In one aspect, the present invention provides oligonucleotide sequences that can be used in nucleic acid amplification tests for the specific detection of either strand of target sequences in the open reading frame-1 (ORF1) gene, cytosine methyltransferase (dcmG) gene or pilin inverting protein homolog (pivNG) gene of *Neisseria gonorrhoeae*.

The ORF1 gene has been described as a genomic region that contains sequences that can be used to discriminate *Neisseria gonorrhoeae* from other *Neisseria* species (C. G. Miyada and T. L. Born, Mol. Cell. Probes, 1991, 5: 327-335). The ORF1 gene of *Neisseria gonorrhoeae* has also been reported to have significant homology to cytosine DNA methyltransferases (C. G. Miyada and T. L. Born, Mol. Cell. Probes, 1991, 5: 327-335), such as the cytosine methyltransferase (dcmG) gene (J. F. Dempsey et al., J. Bacteriol., 1991, 173: 5476-5486; J. A. F. Dempsey and J. G. Cannon, J. Bacteriol., 1994, 176: 2055-2060). The pivNG gene is found in multiple copies on the *Neisseria gonorrhoeae* chromosome. Silica analysis of the fully sequenced genome of *Neisseria gonorrhoeae* strain FA1090 and additional Southern blot analyses have demonstrated that there are eight copies of the gene clustered in three separate regions of the *Neisseria gonorrhoeae* chromosome (E. P. Skaar et al., J. Bacteriol., 2005, 187: 1276-1286). These multiple copies have been called invertase-related genes (irg1, NCBI locuslink ID: 3282015; irg2, NCBI locuslink ID: 3282236; irg3, NCBI locuslink ID: 3281824; irg4, NCBI locuslink ID: 3281830; irg5, NCBI locuslink ID: 3281859; irg6, NCBI locuslink ID: 3281314; irg7, NCBI locuslink ID: 3281292; irg8, NCBI locuslink ID: 3282553). The pivNG gene has been reported to contain sequences that can be used to discriminate *Neisseria gonorrhoeae* from other *Neisseria* species (C. S. Carrick et al., Gene, 1998, 220: 21-29).

As mentioned above, the present invention provides oligonucleotide sequences that recognize regions within the ORF1 gene, dcmG gene and pivNG gene of *Neisseria gonorrhoeae*. Exemplary oligonucleotide sequences of the present invention are presented in Table 1 (SEQ. ID NOs. 1 to 52), along with their corresponding map position. These sequences were identified by the present Applicants by sequence alignment with the ORF1 gene sequence, the dcmG gene sequence and the pivNG gene sequence using Vector NTI (Invitrogen Corp., Carlsbad, Calif.), ABI primer express (Applied Biosystems, Foster City, Calif.), and Oligo6 Primer Analysis (Molecular Biology Insights, Inc., Cascade, Calif.) software programs.

As will be appreciated by one skilled in the art, any of the oligonucleotide sequences (or active fragments thereof) disclosed herein for amplification, detection or quantification of *Neisseria gonorrhoeae* may be employed as detection probe or amplification primer, depending on the intended use and/or assay format. For example, an inventive oligonucleotide sequence used as an amplification primer in one assay can be used as a detection probe in a different assay. A given inventive oligonucleotide sequence may be modified, for example, by attaching to the sequence, a specialized sequence (e.g., a promoter sequence) required by the selected amplification method, or by attaching a label (e.g., a fluorescent dye) to facilitate detection. Thus, it is to be understood that an oligonucleotide according to the present invention may include one or more sequences which can serve as spacers, linkers, sequences for labeling or binding to an enzyme, which may impart added stability or susceptibility to degradation process or other desirable property to the oligonucleotide.

Based on the oligonucleotide sequences provided by the present invention, one or more oligonucleotide analogues can be prepared (see below). Such analogues may contain alternative structures such as peptide nucleic acids or "PNAs" (i.e., molecules with a peptide-like backbone instead of the phosphate sugar backbone of naturally occurring nucleic acids) and the like. These alternative structures, representing the sequence of the present invention, are likewise part of the present invention. Similarly, it is understood that oligonucleotides consisting of sequences of the present invention may contain deletions, additions and/or substitutions of nucleic acid bases, to the extent that such alterations do not negatively affect the properties of the nucleic acid molecules. In particular, the alterations should not result in significant decrease of the hybridizing properties of the oligonucleotides.

Primer Sets and Primer/Probe Sets

In another aspect, the present invention relates to combinations of oligonucleotide sequences disclosed herein for the detection of *Neisseria gonorrhoeae* in biological samples. More specifically, the present invention provides primer sets and primer/probe sets.

As used herein, the term "primer set" refers to two or more primers which together are capable of priming the amplification of a nucleotide sequence of interest (e.g., a target sequence within the OFR1 gene, the dcmG gene or the pivNG gene of *Neisseria gonorrhea*). In certain embodiments, the term "primer set" refers to a pair of primers including a 5' (upstream) primer (or forward primer) that hybridizes with the 5'-end of the nucleic acid sequence to be amplified and a 3' (downstream) primer (or reverse primer) that hybridizes with the complement of the sequence to be amplified. Such primer sets or primer pairs are particularly useful in PCR amplification reactions.

Examples of primer sets comprising a forward amplification primer and a reverse amplification primer include:

Primer Set 1, which comprises a forward primer comprising SEQ. ID NO. 1 (5'-GCGGATTCCCTTGTCAAGATT-3') or any active fragment thereof, and a reverse primer comprising SEQ. ID NO. 2 (5'-GCCGCGCTCACCCTCTA-3') or any active fragment thereof;

Primer Set 2, which comprises a forward primer comprising SEQ. ID NO. 5 (5'-AGTACGTTTGGATACAG-GATTTGATTT-3') or any active fragment thereof, and a reverse primer comprising SEQ. ID NO. 6 (5'-AGC-CGTTTTCGCCAGTTTC-3') or any active fragment thereof;

Primer Set 3, which comprises a forward primer comprising SEQ. ID NO. 8 (5'-GGAACGAGCCATCAAAAACAA-3') or any active fragment thereof, and a reverse primer comprising SEQ. ID NO. 9 (5'-GCGGTTCAGGGAAGTGATAGC-3') or any active fragment thereof;

Primer Set 4, which comprises a forward primer comprising SEQ. ID NO. 12 (5'-AAGGTATGATTAGCCACGTTTATCG-3') or any active fragment thereof, and a reverse primer comprising SEQ. ID NO. 13 (5'-CGCCACCTGCTGCAATAATT-3') or any active fragment thereof;

Primer Set 5, which comprises a forward primer comprising SEQ. ID NO. 15 (5'-GCCTTTTTTCCTTTCGGGATT-3') or any active fragment thereof, and a reverse primer comprising SEQ. ID NO. 16 (5'-GTACATAAGAAAGGCGGAGATTACG-3') or any active fragment thereof;

Primer Set 6, which comprises a forward primer comprising SEQ. ID NO. 19 (5'-GACGCTTCACGCCTTCCTT-3') or any active fragment thereof, and a reverse primer comprising SEQ. ID NO. 20 (5'-CCATGAATGAACAGCTTGAAGTTT-3') or any active fragment thereof;

Primer Set 7, which comprises a forward primer comprising SEQ. ID NO. 22 (5'-GCATCCTGTTTGTCTGTTTTGG-3') or any active fragment thereof, and a reverse primer comprising SEQ. ID NO. 23 (5'-TTACGTAGTGAATCCGCTGAAAATA-3') or any active fragment thereof;

Primer Set 8, which comprises a forward primer comprising SEQ. ID NO. 25 (5'-CCGAATGCTCCGTTTTGC-3') or any active fragment thereof, and a reverse primer comprising SEQ. ID NO. 26 (5'-GTAACGCCGTAGGATTGGATATATC-3') or any active fragment thereof;

Primer Set 9, which comprises a forward primer comprising SEQ. ID NO. 29 (5'-TGATCTAAACCTTTTGAATCGTTGTC-3') or any active fragment thereof, and a reverse primer comprising SEQ. ID NO. 30 (5'-AACGCATCCGCCATGGT-3') or any active fragment thereof;

Primer Set 10, which comprises a forward primer comprising SEQ. ID NO. 32 (5'-GACGCTTCACGCCTTCCTT-3') or any active fragment thereof, and a reverse primer comprising SEQ. ID. NO. 33 (5'-CCATGAATGAACAGCTTGAAGTTT-3') or any active fragment thereof;

Primer Set 11, which comprises a forward primer comprising SEQ. ID NO. 35 (5'-TCTGCCTATTGCCGGTATGGT-3') or any active fragment thereof, and a reverse primer comprising SEQ. ID NO. 36 (5'-GAAGCGGCCAAAGCATATGC-3') or any active fragment thereof;

Primer Set 12, which comprises a forward primer comprising SEQ. ID NO. 38 (5'-ATTGCCGGTATGGTTTCAA-3') or any active fragment thereof, and a reverse primer comprising SEQ. ID NO. 39 (5'-GAAGCGGCCAAAGCATATGC-3') or any fragment thereof;

Primer Set 13, which comprises a forward primer comprising SEQ. ID NO. 41 (5'-GTCATTCTGCCTATTGCCGGT-3') or any active fragment thereof, and a reverse primer comprising SEQ. ID NO. 42 (5'-GAAGCGGCCAAAGCATATGC-3') or any fragment thereof;

Primer Set 14, which comprises a forward primer comprising SEQ. ID NO. 44 (5'-TCTGCCTATTGCCGGTATGGT-3') or any active fragment thereof, and a reverse primer comprising SEQ. ID NO. 45 (5'-GAAGCGGCCAAAGCATATGC-3') or any active fragment thereof;

Primer Set 15, which comprises a forward primer comprising SEQ. ID NO. 47 (5'-TCTGCCTATTGCCGGTATGGT-3') or any active fragment thereof, and a reverse primer comprising SEQ. ID NO. 48 (5'-GAAGCGGCCAAAGCATATGC-3') or any active fragment thereof; and Primer Set 16, which comprises a forward primer comprising SEQ. ID NO. 50 (5'-TGATCTAAACCTTTTGAATCGTTGTC-3') or any active fragment thereof, and a reverse primer comprising SEQ. ID NO. 51 (5'-GTAACGCCGTAGGATTGGATATATC-3') or any active fragment thereof.

These primer sets can be used according to any nucleic acid amplification technique that employs two or more oligonucleotides to amplify a target sequence (as discussed below). Amplification products produced using an inventive primer set may be detected using any of a variety of detection methods well known in the art. For example, amplification products may be detected using agarose gel electrophoresis and visualization by ethidium bromide staining and exposure to ultraviolet (UV) light or by sequence analysis of the amplification product for confirmation of *Neisseria gonorrhoeae* identity.

Alternatively, probe sequences can be employed using a variety of homogeneous or heterogeneous methodologies to detect amplification products. Generally in such methods, the probe hybridizes to a strand of an amplification product (or amplicon) to form an amplification product/probe hybrid. The hybrid can then be directly or indirectly detected, for example using labels on the probe, primers, or both the probe and primers.

Accordingly, the present invention provides primer/probe sets for the detection of *Neisseria gonorrhoeae* in biological samples. As used herein, the term "primer/probe set" refers to a combination comprising two or more primers which together are capable of priming the amplification of a nucleotide sequence of interest (e.g., a target sequence within the OFR1 gene, the dcmG gene or the pivNG gene of *Neisseria gonorrhoeae*), and at least one probe which can detect the target sequence. The probe generally hybridizes to a strand of an amplification product (or amplicon) to form an amplification product/probe hybrid, which can be detected.

The present invention provides primer/probe sets that can be used according to nucleic acid amplification procedures to specifically amplify and detect *Neisseria gonorrhoeae* target sequences in test samples. The inventive primer/probe sets generally comprise a primer set, as described above, and at least one detection probe, which hybridizes to the amplicon generated by the primer set. The detection probe may comprise a detectable moiety. In certain embodiments, the detection probe comprises a fluorescent moiety attached at the 5' end and a quencher moiety attached at the 3' end (see below).

Examples of Primer/Probe Sets Include:

Primer/Probe Set 1, which comprises a forward primer comprising SEQ. ID NO. 1 (5'-GCGGATTCCCTTGTCAAGATT-3') or an active fragment thereof, a reverse primer comprising SEQ. ID NO. 2 (5'-GCCGCGCTCACCCTCTA-3') or an active fragment thereof; a complementary detection probe comprising SEQ. ID NO. 3 (5'-TTCCATGATTTGGAAACAGCCGGG-3') or an active fragment thereof; and a reverse complementary detection probe comprising SEQ. ID NO. 4 (5'-CCCGGCTGTTTCCAAATCATGGAA-3') or an active fragment thereof;

Primer/Probe Set 2, which comprises a forward primer comprising SEQ. ID NO. 5 (5'-AGTACGTTTGGATACAGGATTTGATT-3') or an active fragment thereof, a reverse primer comprising SEQ. ID NO. 6 (5'-AGCCGTTTTCGCCAGTTTC-3') or an active fragment thereof, and a complementary detection probe comprising SEQ. ID NO. 7 (5'-CCATCCGGAACCGACGCACAA-3') or an active fragment thereof;

Primer/Probe Set 3, which comprises a forward primer comprising SEQ. ID NO. 8 (5'-GGAACGAGCCATCAAAAACAA-3') or an active fragment thereof, a reverse primer comprising SEQ. ID NO. 9 (5'-GCGGTTCAGG-GAAGTGATAGC-3') or an active fragment thereof, a complementary detection probe comprising SEQ. ID NO. 10 (5'-TTGCAGCAGGTGGCGGTGGTACTT-3') or an active fragment thereof, and a reverse complementary detection probe comprising SEQ. ID NO. 11 (5'-AAGTACCACCGC-CACCTGCTGCAA-3') or an active fragment thereof;

Primer/Probe Set 4, which comprises a forward primer comprising SEQ. ID NO. 12 (5'-AAGGTATGATTAGC-CACGTTTATCG-3') or an active fragment thereof; a reverse primer comprising SEQ. ID NO. 13 (5'-CGCCACCTGCTG-CAATAATT-3') or an active fragment thereof; and a complementary detection probe comprising SEQ. ID NO. 14 (5'-CGTATGCATCGGAACGAGCCATCAAA-3') or an active fragment thereof;

Primer/Probe Set 5, which comprises a forward primer comprising SEQ. ID NO. 15 (5'-GCCTTTTTTCCTTTCGG-GATT-3') or an active fragment thereof; a reverse primer comprising SEQ. ID NO. 16 (5'-GTACATAAGAAAGGCG-GAGATTACG-3') or an active fragment thereof; a complementary detection probe comprising SEQ. ID NO. 17 (5'-ACGCCGATTTGTAACGCGATGGA-3') or an active fragment thereof; and a reverse complementary detection probe comprising SEQ. ID NO. 18 (5'-TCCATCGCGTTA-CAAATCGGCGT-3') or an active fragment thereof;

Primer/Probe Set 6, which comprises a forward primer comprising SEQ. ID. NO. 19 (5'-GACGCTTCACGCCTTC-CTT-3') or an active fragment thereof; a reverse primer comprising SEQ. ID NO. 20 (5'-CCATGAATGAACAGCT-TGAAGTTT-3') or an active fragment thereof; and a complementary detection probe comprising SEQ. ID NO. 21 (5'-AGGCTTCTCCGTCTGCTCTTTTATCTTCTCCTT-3') or an active fragment thereof;

Primer/Probe Set 7, which comprises a forward primer comprising SEQ. ID NO. 22 (5'-GCATCCTGTTTGTCT-GTTTTGG-3') or an active fragment thereof; a reverse primer comprising SEQ. ID NO. 23 (5'-TTACGTAGTGAATC-CGCTGAAAATA-3') or an active fragment thereof; and a complementary detection probe comprising SEQ. ID NO. 24 (5'-CGCTTGAACCTGCTTTCTGCATACTTGC-3') or an active fragment thereof;

Primer/Probe Set 8, which comprises a forward primer comprising SEQ. ID NO. 25 (5'-CCGAATGCTC-CGTTTTGC-3') or an active fragment thereof; a reverse primer comprising SEQ. ID NO. 26 (5'-GTAACGCCGTAG-GATTGGATATATC-3') or an active fragment thereof a complementary detection probe comprising SEQ. ID NO. 27 (5'-CCATGGCGGATGCGTTAAAGGTCAG-3') or an active fragment thereof; and a reverse complementary detection probe comprising SEQ. ID NO. 28 (5'-CTGACCTT-TAACGCATCCGCCATGG-3') or an active fragment thereof;

Primer/Probe Set 9, which comprises a forward primer comprising SEQ. ID NO. 29 (5'-TGATCTAAAC-CTTTTGAATCGTTGTC-3') or an active fragment thereof; a reverse primer comprising SEQ. ID NO. 30 (5'-AACGCATC-CGCCATGGT-3') or an active fragment thereof; and a complementary detection probe comprising SEQ. ID NO. 31 (5'-AACTTTGCCGAATGCTCCGTTTTGC-3') or an active fragment thereof;

Primer/Probe Set 10, which comprises a forward primer comprising SEQ. ID NO. 32 (5'-GACGCTTCACGCCTTC-CTT-3') or an active fragment thereof; a reverse primer comprising SEQ. ID NO. 33 (5'-CCATGAATGAACAGCT-TGAAGTTT-3') or an active fragment thereof; and a detection probe comprising SEQ. ID NO. 34 (5'-AGGCT-TCTCCGTCTGCTCT-3') or an active fragment thereof;

Primer/Probe Set 11, which comprises a forward primer comprising SEQ. ID NO. 35 (5'-TCTGCCTATTGCCGG-TATGGT-3') or an active fragment thereof; a reverse primer comprising SEQ. ID NO. 36 (5'-GAAGCGGCCAAAG-CATATGC-3') or an active fragment thereof; and a detection probe comprising SEQ. ID NO. 37 (5'-AGGCTTCTC-CGTCTGCTCT-3') or an active fragment thereof;

Primer/Probe Set 12, which comprises a forward primer comprising SEQ. ID NO. 38 (5'-ATTGCCGGTATG-GTTTCAA-3') or an active fragment thereof; a reverse primer comprising SEQ. ID NO. 39 (5'-GAAGCGGC-CAAAGCATATGC-3') or an active fragment thereof; and a detection probe comprising SEQ. ID NO. 40 (5'-AGGCT-TCTCCGTCTGCTCT 3') or an active fragment thereof;

Primer/Probe Set 13, which comprises a forward primer comprising SEQ. ID NO. 41 (5'-GTCATTCTGCCTATTGC-CGGT-3') or an active fragment thereof; a reverse primer comprising SEQ. ID NO. 42 (5'-GAAGCGGCCAAAG-CATATGC-3') or an active fragment thereof; and a detection probe comprising SEQ. ID NO. 43 (5'-TGCATCCAATCA-GATTTCCTTTCG-3') or an active fragment thereof;

Primer/Probe Set 14, which comprises a forward primer comprising SEQ. ID NO. 44 (5'-TCTGCCTATTGCCGG-TATGGT-3') or an active fragment thereof; a reverse primer comprising SEQ. ID NO. 45 (5'-GAAGCGGCCAAAG-CATATGC-3') or an active fragment thereof; and a detection probe comprising SEQ. ID No. 46 (5'-GCTTCACGCCTTC-CTTGCAGTTA-3') or an active fragment thereof;

Primer/Probe Set 15, which comprises a forward primer comprising SEQ. ID NO. 47 (5'-TCTGCCTATTGCCGG-TATGGT-3') or an active fragment thereof; a reverse primer comprising SEQ. ID NO. 48 (5'-GAAGCGGCCAAAG-CATATGC-3') or an active fragment thereof; and a detection probe comprising SEQ. ID No. 49 (5'-TCACGCCTTCCT-TGCAGTTA-3') or an active fragment thereof; and Primer/Probe Set 16, which comprises a forward primer comprising SEQ. ID NO. 50 (5'-TGATCTAAAC-CTTTTGAATCGTTGTC-3') or an active fragment thereof; a reverse primer comprising SEQ. ID NO. 51 (5'-GTAACGC-CGTAGGATTGGATATATC-3') or an active fragment thereof; and a detection probe comprising SEQ. ID No. 52 (5'-CCATGGCGGATGCGTTAAAGGTCAG-3') or an active fragment thereof.

Oligonucleotide Preparation

Oligonucleotides of the invention may be prepared by any of a variety of methods well known in the art (see, for example, J. Sambrook et al., "*Molecular Cloning. A Laboratory Manual*", 1989, 2nd Ed., Cold Spring Harbour Laboratory Press: New York, N.Y.; "*PCR Protocols. A Guide to Methods and Applications*", 1990, M. A. Innis (Ed.), Academic Press: New York, N.Y.; P. Tijssen "*Hybridization with Nucleic Acid Probes—Laboratory Techniques in Biochemistry and Molecular Biology (Parts I and II)*", 1993, Elsevier Science; "*PCR Strategies*", 1995, M. A. Innis (Ed.), Academic Press: New York, N.Y.; and "*Short Protocols in Molecular Biology*", 2002, F. M. Ausubel (Ed.), 5th Ed., John Wiley & Sons: Secaucus, N.J.). For example, oligonucleotides may be prepared by chemical synthesis and polymerization based on a template as described, e.g., in S. A. Narang et al., Meth. Enzymol. 1979, 68: 90-98; E. L. Brown et al., Meth. Enzymol. 1979, 68: 109-151; E. S. Belousov et al., Nucleic Acids Res. 1997, 25: 3440-3444; D. Guschin et al., Anal. Biochem. 1997, 250: 203-211; M. J. Blommers et al., Biochemistry, 1994, 33: 7886-7896; and K. Frenkel et al., Free Radic. Biol. Med. 1995, 19: 373-380; and U.S. Pat. No. 4,458,066).

For example, oligonucleotides may be prepared using an automated, solid-phase procedure based on the phosphoramidite approach. In such a method, each nucleotide is individually added to the 5'-end of a growing oligonucleotide chain, which is attached at the 3'-end to a solid support. The added nucleotides are in the form of trivalent 3'-phosphoramidites that are protected by a dimethoxytriyl (or DMT) group at the 5' position. After base-induced phosphoramidite coupling, mild oxidation to give a pentavalent phosphotriester intermediate and DMT removal provides a new site for oligonucleotide elongation. The oligonucleotides are then cleaved off the solid support, and the phosphodiester and exocyclic amino groups are deprotected with ammonium hydroxide. These syntheses may be performed on oligo synthesizers such as those commercially available from Perkin Elmer/Applied Biosystems, Inc. (Foster City, Calif.), DuPont (Wilmington, Del.) or Milligen (Bedford, Mass.). Alternatively, oligonucleotides can be custom made and ordered from a variety of commercial sources well-known in the art, including, for example, the Midland Certified Reagent Company (Midland, Tex.), ExpressGen, Inc. (Chicago, Ill.), Operon Technologies, Inc. (Huntsville, Ala.), BioSearch Technologies, Inc. (Novato, Calif.), and many others.

Purification of oligonucleotides of the invention, where necessary or desired, may be carried out by any of a variety of methods well-known in the art. Purification of oligonucleotides is typically performed either by native acrylamide gel electrophoresis, by anion-exchange HPLC as described, for example, by J. D. Pearson and F. E. Regnier (J. Chrom., 1983, 255: 137-149) or by reverse phase HPLC (G. D. McFarland and P. N. Borer, Nucleic Acids Res., 1979, 7: 1067-1080).

The sequence of oligonucleotides can be verified using any suitable sequencing method including, but not limited to, chemical degradation (A. M. Maxam and W. Gilbert, Methods of Enzymology, 1980, 65: 499-560), matrix-assisted laser desorption ionization time-of-flight (MALDI-TOF) mass spectrometry (U. Pieles et al., Nucleic Acids Res., 1993, 21: 3191-3196), mass spectrometry following a combination of alkaline phosphatase and exonuclease digestions (H. Wu and H. Aboleneen, Anal. Biochem., 2001, 290: 347-352), and the like.

As already mentioned above, modified oligonucleotides may be prepared using any of several means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc), or charged linkages (e.g., phosphorothioates, phosphorodithioates, etc). Oligonucleotides may contain one or more additional covalently linked moieties, such as, for example, proteins (e.g., nucleases, toxins, antibodies, signal peptides, poly-L-lysine, etc), intercalators (e.g., acridine, psoralen, etc), chelators (e.g., to chelate metals, radioactive metals, oxidative metals, etc), and alkylators. Oligonucleotides may also be derivatized by formation of a methyl or ethyl phosphotriester or an alkyl phosphoramidate linkage. Furthermore, the oligonucleotide sequences of the present invention may also be modified with a label.

Labeling of Oligonucleotide Sequences

In certain embodiments, detection probes or amplification primers or both probes and primers are labeled with a detectable agent or moiety before being used in amplification/detection assays. In some embodiments, the detection probes are labeled with a detectable agent. The role of a detectable agent is to allow visualization and detection of amplified target sequences (amplicons). Preferably, the detectable agent is selected such that it generates a signal which can be measured and whose intensity is related (e.g., proportional) to the amount of amplification products in the sample being analyzed.

The association between an oligonucleotide (e.g., detection probe) and detectable agent can be covalent or non-covalent. Labeled detection probes can be prepared by incorporation of, or conjugation to, a detectable moiety. Labels can be attached directly to the nucleic acid sequence or indirectly (e.g., through a linker). Linkers or spacer arms of various lengths are known in the art and are commercially available, and can be selected to reduce steric hindrance, or to confer other useful or desired properties to the resulting labeled molecules (see, for example, E. S. Mansfield et al., Mol. Cell. Probes, 1995, 9: 145-156).

Methods for labeling nucleic acid molecules are well-known in the art. For a review of labeling protocols, label detection techniques, and recent developments in the field, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35: 135-153. Standard nucleic acid labeling methods include: incorporation of radioactive agents, direct attachments of fluorescent dyes (L. M. Smith et al., Nucl. Acids Res., 1985, 13: 2399-2412) or of enzymes (B. A. Connoly and O. Rider, Nucl. Acids. Res., 1985, 13: 4485-4502); chemical modifications of nucleic acid molecules making them detectable immunochemically or by other affinity reactions (T. R. Broker et al., Nucl. Acids Res. 1978, 5: 363-384; E. A. Bayer et al., Methods of Biochem. Analysis, 1980, 26: 1-45; R. Langer et al., Proc. Natl. Acad. Sci. USA, 1981, 78: 6633-6637; R. W. Richardson et al., Nucl. Acids Res. 1983, 11: 6167-6184; D. J. Brigati et al., Virol. 1983, 126: 32-50; P. Tchen et al., Proc. Natl. Acad. Sci. USA, 1984, 81: 3466-3470; J. E. Landegent et al., Exp. Cell Res. 1984, 15: 61-72; and A. H. Hopman et al., Exp. Cell Res. 1987, 169: 357-368); and enzyme-mediated labeling methods, such as random priming, nick translation, PCR and tailing with terminal transferase (for a review on enzymatic labeling, see, for example, J. Temsamani and S. Agrawal, Mol. Biotechnol. 1996, 5: 223-232). More recently developed nucleic acid labeling systems include, but are not limited to: ULS (Universal Linkage System), which is based on the reaction of monoreactive cisplatin derivatives with the N7 position of guanine moieties in DNA (R. J. Heetebrij et al., Cytogenet. Cell. Genet. 1999, 87: 47-52), psoralen-biotin, which intercalates into nucleic acids and upon UV irradiation becomes covalently bonded to the nucleotide bases (C. Levenson et al., Methods Enzymol. 1990, 184: 577-583; and C. Pfannschmidt et al., Nucleic Acids Res. 1996, 24: 1702-1709), photoreactive azido derivatives (C. Neves et al., Bioconjugate Chem. 2000, 11: 51-55), and DNA alkylating agents (M. G. Sebestyen et al., Nat. Biotechnol. 1998, 16: 568-576).

Any of a wide variety of detectable agents can be used in the practice of the present invention. Suitable detectable agents include, but are not limited to, various ligands, radionuclides (such as, for example, $^{32}P$, $^{35}S$, $^{3}H$, $^{14}C$, $^{125}I$, $^{131}I$, and the like); fluorescent dyes (for specific exemplary fluorescent dyes, see below); chemiluminescent agents (such as, for example, acridinium esters, stabilized dioxetanes, and the like); spectrally resolvable inorganic fluorescent semiconductor nanocrystals (i.e., quantum dots), metal nanoparticles (e.g., gold, silver, copper and platinum) or nanoclusters; enzymes (such as, for example, those used in an ELISA, i.e., horseradish peroxidase, beta-galactosidase, luciferase, alkaline phosphatase); colorimetric labels (such as, for example, dyes, colloidal gold, and the like); magnetic labels (such as, for example, Dynabeads™); and biotin, dioxigenin or other haptens and proteins for antisera or monoclonal antibodies are available.

In certain embodiments, the inventive detection probes are fluorescently labeled. Numerous known fluorescent labeling moieties of a wide variety of chemical structures and physical characteristics are suitable for use in the practice of this invention. Suitable fluorescent dyes include, but are not limited to, fluorescein and fluorescein dyes (e.g., fluorescein isothiocyanine or FITC, naphthofluorescein, 4',5'-dichloro-2',7'-dimethoxy-fluorescein, 6-carboxyfluorescein or FAM), carbocyanine, merocyanine, styryl dyes, oxonol dyes, phycoerythrin, erythrosin, eosin, rhodamine dyes (e.g., carboxytetramethylrhodamine or TAMRA, carboxyrhodamine 6G, carboxy-X-rhodamine (ROX), lissamine rhodamine B, rhodamine 6G, rhodamine Green, rhodamine Red, tetramethylrhodamine or TMR), coumarin and coumarin dyes (e.g., methoxycoumarin, dialkylaminocoumarin, hydroxycoumarin and aminomethylcoumarin or AMCA), Oregon Green Dyes (e.g., Oregon Green 488, Oregon Green 500, Oregon Green 514), Texas Red, Texas Red-X, Spectrum Red™, Spectrum Green™, cyanine dyes (e.g., Cy-3™, Cy-5™, Cy-3.5™, Cy-5.5™), Alexa Fluor dyes (e.g., Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), IRDyes (e.g., IRD40, IRD 700, IRD 800), and the like. For more examples of suitable fluorescent dyes and methods for linking or incorporating fluorescent dyes to nucleic acid molecules see, for example, "*The Handbook of Fluorescent Probes and Research Products*", 9$^{th}$ Ed., Molecular Probes, Inc., Eugene, Oreg. Fluorescent dyes as well as labeling kits are commercially available from, for example, Amersham Biosciences, Inc. (Piscataway, N.J.), Molecular Probes Inc. (Eugene, Oreg.), and New England Biolabs Inc. (Beverly, Mass.).

Rather than being directly detectable themselves, some fluorescent groups (donors) transfer energy to another fluorescent group (acceptor) in a process of fluorescent resonance energy transfer (FRET), and the second group produces the detectable fluorescent signal. In these embodiments, the oligonucleotide detection probe may, for example, become detectable when hybridized to an amplified target sequence. Examples of FRET acceptor/donor pairs suitable for use in the present invention include, but are not limited to, fluorescein/tetramethylrhodamine, IAEDANS/FITC, IAEDANS/5-(iodoacetomido)fluorescein, B-phycoerythrin/Cy-5, and EDANS/Dabcyl.

The use of physically linked fluorescent reporter/quencher molecule pairs is also within the scope of the invention. The use of such systems in TaqMan™ assays (as described, for example, in U.S. Pat. Nos. 5,210,015; 5,804,375; 5,487,792 and 6,214,979) or as Molecular Beacons (as described, for example in, S. Tyagi and F. R. Kramer, Nature Biotechnol. 1996, 14: 303-308; S. Tyagi et al., Nature Biotechnol. 1998, 16: 49-53; L. G. Kostrikis et al., Science, 1998, 279: 1228-1229; D. L. Sokol et al., Proc. Natl. Acad. Sci. USA, 1998, 95: 11538-11543; S. A. Marras et al., Genet. Anal. 1999, 14: 151-156; and U.S. Pat. Nos. 5,846,726, 5,925,517, 6,277,581 and 6,235,504) is well-known in the art. With the TaqMan™ assay format, products of the amplification reaction can be detected as they are formed in a so-called "real-time" manner. As a result, amplification product/probe hybrids are formed and detected while the reaction mixture is under amplification conditions.

In some embodiments of the present invention, the PCR detection probes are

TaqMan™-like probes that are labeled at the 5'-end with a fluorescent moiety and at the 3'-end with a quencher moiety. Suitable fluorophores and quenchers for use with TaqMan™-like probes are disclosed in U.S. Pat. Nos. 5,210,015; 5,804, 375; 5,487,792; and 6,214,979; and WO 01/86001 (each of which is incorporated herein by reference in its entirety). Examples of quenchers include, but are not limited to DABCYL (i.e., 4-(4'-dimethylaminophenylazo)-benzoic acid) succinimidyl ester, diarylrhodamine carboxylic acid, succinimidyl ester (or QSY-7), and 4',5'-dinitrofluorescein carboxylic acid, succinimidyl ester (or QSY-33) (all available, for example, from Molecular Probes), quencher1 (Q1; available from Epoch Biosciences, Bothell, Wash.), or BLACK HOLE QUENCHER™ reagents, such as quenchers BHQ-1, BHQ-2, and BHQ-3 (available from BioSearch Technologies, Inc., Novato, Calif.). In certain embodiments, the PCR detection probes are TaqMan™-like probes that are labeled at the 5' end with FAM and at the 3' end with a BLACK HOLE QUENCHER™ reagent.

A "tail" of normal or modified nucleotides can also be added to oligonucleotide probes for detectability purposes. A second hybridization with nucleic acid complementary to the tail and containing one or more detectable labels (such as, for example, fluorophores, enzymes or bases that have been radioactively labeled) allows visualization of the amplicon/probe hybrids (see, for example, the system commercially available from Enzo Biochem. Inc., New York, N.Y.). Another example of an assay with which the inventive oligonucleotides are useful is a signal amplification method such as that described in U.S. Pat. No. 5,124,246 (which is incorporated herein by reference in its entirety). In that method, the signal is amplified through the use of amplification multimers, polynucleotides which are constructed so as to contain a first segment that hybridizes specifically to the "tail" added to the oligonucleotide probes, and a multiplicity of identical second segments that hybridize specifically to a labeled probe. The degree of amplification is theoretically proportional to the number of iterations of the second segment. The multimers may be either linear or branched. Branched multimers may be in the shape of a fork or a comb.

The selection of a particular nucleic acid labeling technique will depend on the situation and will be governed by several factors, such as the ease and cost of the labeling method, the quality of sample labeling desired, the effects of the detectable moiety on the hybridization reaction (e.g., on the rate and/or efficiency of the hybridization process), the nature of the amplification method used, the nature of the detection system, the nature and intensity of the signal generated by the detectable label, and the like.

Amplification of *Neisseria gonorrhoeae* Target Sequences Using Inventive Primers The use of oligonucleotide sequences of the present invention to amplify *Neisseria gonorrhoeae* target sequences in test samples is not limited to any particular nucleic acid amplification technique or any particular modification thereof. In fact, oligonucleotide sequences of the present invention can be employed in any of a variety of nucleic acid amplification methods well-known in the art (see, for example, A. R. Kimmel and S. L. Berger, Methods Enzymol. 1987, 152: 307-316; J. Sambrook et al., "*Molecular Cloning.*

*A Laboratory Manual"*, 1989, 2$^{nd}$ Ed., Cold Spring Harbour Laboratory Press: New York, N.Y.; *"Short Protocols in Molecular Biology"*, F. M. Ausubel (Ed.), 2002, 5$^{th}$ Ed., John Wiley & Sons: Secaucus, N.J.).

Such nucleic acid amplification methods include, but are not limited to the Polymerase Chain Reaction (or PCR, described in, for example, *"PCR Protocols: A Guide to Methods and Applications"*, M. A. Innis (Ed.), 1990, Academic Press: New York; *"PCR Strategies"*, M. A. Innis (Ed.), 1995, Academic Press: New York; *"Polymerase chain reaction: basic principles and automation in PCR. A Practical Approach"*, McPherson et al. (Eds.), 1991, IRL Press: Oxford; Saiki et al., Nature, 1986, 324: 163; and U.S. Pat. Nos. 4,683,195, 4,683,202 and 4,889,818, each of which is incorporated herein by reference in its entirety); and variations thereof including TaqMan™-based assays (Holland et al., Proc. Natl. Acad. Sci., 1991, 88: 7276-7280), and reverse transcriptase polymerase chain reaction (or RT-PCR, described in, for example, U.S. Pat. Nos. 5,322,770 and 5,310,652, each of which is incorporated herein by reference in its entirety).

In PCR, a pair of primers is employed in excess to hybridize to the complementary strands of the target nucleic acid. The primers are each extended by a DNA polymerase using the target sequence as a template. The extension products become target themselves after dissociation (denaturation) from the original target strand. New primers are then hybridized and extended by the polymerase, and the cycle is repeated to exponentially increase the number of copies of amplicons. Examples of DNA polymerases capable of producing primer extension products in PCR reactions include, but are not limited to: *E. coli* DNA polymerase I, Klenow fragment of DNA polymerase I, T4 DNA polymerase, thermostable DNA polymerases isolated from *Thermus aquaticus* (Taq), available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). RNA target sequences may be amplified by reverse transcribing the mRNA into cDNA, and then performing PCR (RT-PCR), as described above. Alternatively, a single enzyme may be used for both steps as described in U.S. Pat. No. 5,322,770 (which is incorporated herein by reference in its entirety).

In addition to the enzymatic thermal amplification methods described above, isothermal enzymatic amplification reactions can be employed to amplify *Neisseria gonorrhoeae* target sequences using oligonucleotide primers of the present invention (S. C. Andras et al., Mol. Biotechnol., 2001, 19: 29-44). These methods include, but are not limited to, Transcription-Mediated Amplification (or TMA, described in, for example, D. Y. Kwoh et al., Proc. Natl. Acad. Sci. USA, 1989, 86: 1173-1177; C. Giachetti et al., J. Clin. Microbiol., 2002, 40: 2408-2419; and U.S. Pat. No. 5,399,491); Self-Sustained Sequence Replication (or 3SR, described in, for example, J. C. Guatelli et al., Proc. Natl. Acad. Sci. USA, 1990, 87: 1874-1848; and E. Fahy et al., PCR Methods and Applications, 1991, 1: 25-33); Nucleic Acid Sequence Based Amplification (or NASBA, described in, for example, T. Kievits et al., J. Virol., Methods, 1991, 35: 273-286; and U.S. Pat. No. 5,130,238) and Strand Displacement Amplification (or SDA, described in, for example, G. T. Walker et al., PNAS, 1992, 89: 392-396; EP 0 500 224 A2). Each of the references cited in this paragraph is incorporated herein by reference in its entirety.

Strand-displacement amplification (SDA) combines the ability of a restriction endonuclease to nick the unmodified strand of its target DNA and the action of an exonuclease-deficient DNA polymerase to extend the 3' end at the nick and displace the downstream DNA strand at a fixed temperature (G. T. Walker et al., Proc. Natl. Acad. Sci. USA, 1992, 89: 392-396). Primers used in SDA include a restriction endonuclease recognition at site 5' to the target binding sequence (U.S. Pat. Nos. 5,270,184 and 5,344,166, each of which is incorporated herein by reference in its entirety).

Nucleic Acid Sequence Based Amplification (NASBA) uses three enzymes (e.g., RNase H, avian myeloblastosis virus (AMV) reverse transcriptase and T7 RNA polymerase) working in concert at a low isothermal temperature, generally 41° C. (J. Compton, Nature, 1991, 350: 91-92; A. B. Chan and J. D. Fox, Rev. Med. Microbiol., 1999, 10: 185-196). The product of a NASBA reaction is mainly single-stranded RNA. The Self Sustaining Sequence Replication (3SR) reaction is a very efficient method for isothermal amplification of target DNA or RNA sequences. A 3SR system involves the collective activities of AMV reverse transcriptase, *E. Coli* RNase H, and DNA-dependent RNA polymerase (e.g., T7 RNA polymerase). Transcription-Mediated Amplification (TMA) uses an RNA polymerase to make RNA from a promoter engineered in the primer region, a reverse transcriptase to produce complementary DNA from the RNA templates and RNase H to remove the RNA from cDNA (J. C. Guatelli et al., Proc. Natl. Acad. Sci. USA, 1990, 87: 1874-1878).

NASBA, 3SR, and TMA primers require an RNA polymerase promoter linked to the target binding sequence of the primer. Promoters or promoter sequences for incorporation in the primers are nucleic acid sequences (either naturally occurring, produced synthetically or a product of a restriction digest) that are specifically recognized by an RNA polymerase that recognizes and binds to that sequence and initiates the process of transcription whereby RNA transcripts are generated. Examples of useful promoters include those which are recognized by certain bacteriophage polymerases such as those from bacteriophage T3, T7 or SP6 or a promoter from *E. coli*.

Detection of Amplified *Neisseria gonorrhoeae* Target Sequences

In certain embodiments of the present invention, oligonucleotide probe sequences are used to detect amplification products generated by the amplification reaction (i.e., amplified *Neisseria gonorrhoeae* target sequence). The inventive probe sequences can be employed using a variety of well-known homogeneous or heterogeneous methodologies.

Homogeneous detection methods include, but are not limited to, the use of FRET labels that are attached to probes and that emit a signal in the presence of the target sequence, Molecular Beacons (S. Tyagi and F. R. Kramer, Nature Biotechnol. 1996, 14: 303-308; S. Tyagi et al., Nature Biotechnol. 1998, 16: 49-53; L. G. Kostrikis et al., Science, 1998, 279: 1228-1229; D. L. Sokol et al., Proc. Natl. Acad. Sci. USA, 1998, 95: 11538-11543; S. A. Marras et al., Genet. Anal. 1999, 14: 151-156; and U.S. Pat. Nos. 5,846,726, 5,925,517, 6,277,581 and 6,235,504), and so-called TaqMan™ assays (U.S. Pat. Nos. 5,210,015; 5,804,375; 5,487,792 and 6,214,979 and WO 01/86001). Using these detection techniques, products of the amplification reaction can be detected as they are formed, i.e., in a so-called real time manner. As a result, amplification product/probe hybrids are formed and detected while the reaction mixture is under amplification conditions.

In certain embodiments, the detection probes of the present invention are used in a TaqMan™ assay. A TaqMan™ assay, also known as fluorogenic 5' nuclease assay, is a powerful and versatile PCR-based detection system for nucleic acid targets.

Analysis is performed in conjunction with thermal cycling by monitoring the generation of fluorescence signals. The assay system has the capability of generating quantitative data allowing the determination of target copy numbers. For example, standard curves can be generated using serial dilutions of previously quantified suspensions of *Neisseria gonorrhoeae*, against which unknown samples can be compared. The TaqMan™ assay is conveniently performed using, for example, AmpliTaq Gold™ DNA polymerase, which has endogenous 5' nuclease activity, to digest an oligonucleotide probe labeled with both a fluorescent reporter dye and a quencher moiety, as described above. Assay results are obtained by measuring changes in fluorescence that occur during the amplification cycle as the probe is digested, uncoupling the fluorescent and quencher moieties and causing an increase in the fluorescence signal that is proportional to the amplification of the target sequence.

Other examples of homogeneous detection methods include hybridization protection assays (HPA). In such assays, the probes are labeled with acridinium ester (AE), a highly chemiluminescent molecule (Weeks et al., Clin. Chem., 1983, 29: 1474-1479; Berry et al., Clin. Chem., 1988, 34: 2087-2090), using a non-nucleotide-based linker arm chemistry (U.S. Pat. Nos. 5,585,481 and 5,185,439). Chemiluminescence is triggered by AE hydrolysis with alkaline hydrogen peroxide, which yields an excited N-methyl acridone that subsequently deactivates with emission of a photon. In the absence of a target sequence, AE hydrolysis is rapid. However, the rate of AE hydrolysis is greatly reduced when the probe is bound to the target sequence. Thus, hybridized and un-hybridized AE-labeled probes can be detected directly in solution, without the need for physical separation.

Heterogeneous detection systems are well-known in the art and generally employ a capture agent to separate amplified sequences from other materials in the reaction mixture. Capture agents typically comprise a solid support material (e.g., microtiter wells, beads, chips, and the like) coated with one or more specific binding sequences. A binding sequence may be complementary to a tail sequence added to oligonucleotide probes of the invention. Alternatively, a binding sequence may be complementary to a sequence of a capture oligonucleotide, itself comprising a sequence complementary to a tail sequence of an inventive oligonucleotide probe. After separation of the amplification product/probe hybrids bound to the capture agents from the remaining reaction mixture, the amplification product/probe hybrids can be detected using any detection methods, such as those described herein.

II—Methods of Detection of *Neisseria gonorrhoeae* in Test Samples

In another aspect, the present invention provides methods for detecting the presence of *Neisseria gonorrhoeae* in a test sample. The inventive methods may be used to test patients who may or may not exhibit symptoms of gonococcal infection or its sequelae, and/or to screen at-risk populations.

Typically, methods of the invention comprise steps of: providing a test sample suspected of containing a *Neisseria gonorrhoeae* nucleic acid (e.g., a nucleic acid comprising a sequence within the open reading frame-1 (ORF1) gene, the cytosine methyltransferase (dcmG) gene or the pilin inverting protein homolog (pivNG) gene of *Neisseria gonorrhoeae*); contacting the test sample with at least one oligonucleotide disclosed herein, such that the oligonucleotide can hybridize to the *Neisseria gonorrhoeae* nucleic acid, if present in the test sample; and detecting any oligonucleotide hybridized to the *Neisseria gonorrhoeae* nucleic acid, wherein the detection of hybridization of the oligonucleotide to the *Neisseria gonorrhoeae* nucleic acid indicates the presence of *Neisseria gonorrhoeae* in the test sample.

Other methods of the present invention comprise contacting a test sample suspected of containing a *Neisseria gonorrhoeae* nucleic acid with at least one primer set or primer/probe set disclosed herein and amplification reaction reagents to form a reaction mixture. The reaction mixture is then placed under amplification conditions so as to amplify the *Neisseria gonorrhoeae* nucleic acid, if present in the test sample, and generate an amplification product. The resulting amplification product may be detected using a variety of detection technologies. In certain embodiments, an amplification product/probe hybrid is formed using a detection probe of the present invention, and detection of such an hybrid indicates the presence of *Neisseria gonorrhoeae* in the test sample.

Sample Preparation

According to methods of the present invention, the presence of *Neisseria gonorrhoeae* in a test sample can be determined by detecting any *Neisseria gonorrhoeae* nucleic acid comprising a sequence within the open reading frame-1 (ORF1) gene, the cytosine methyltransferase (dcmG) gene or the pilin inverting protein homolog (pivNG) gene of *Neisseria gonorrhoeae*. Thus, any liquid or solid biological material suspected of comprising such *Neisseria gonorrhoeae* target sequences can be a suitable test sample. In certain embodiments, preferred test samples include urine (e.g., first void urine), seminal fluid, saliva, ocular lens fluid, lymphatic fluid, endocervical, urethral, rectal, vaginal, vulva-vaginal, and nasopharyngeal samples. Other preferred test samples include PAPS-smear specimens.

Test samples will often be obtained or isolated from patients suspected of being infected with *Neisseria gonorrhoeae*. As already mentioned, a test sample may be used without further treatment after isolation or, alternatively, it may be processed before analysis. For example, a test sample may be treated so as to release *Neisseria gonorrhoeae* nucleic acids from cells that contain them. Methods of nucleic acid extraction are well-known in the art and include chemical methods, temperature methods, and mechanical methods (see, for example, J. Sambrook et al., "*Molecular Cloning: A Laboratory Manual*", 1989, 2$^{nd}$ Ed., Cold Spring Harbour Laboratory Press: New York, N.Y.). There are also numerous different and versatile kits that can be used to extract nucleic acids from biological samples that are commercially available from, for example, Amersham Biosciences (Piscataway, N.J.), BD Biosciences Clontech (Palo Alto, Calif.), Epicentre Technologies (Madison, Wis.), Gentra Systems, Inc. (Minneapolis, Minn.), MicroProbe Corp. (Bothell, Wash.), Organon Teknika (Durham, N.C.), and Qiagen Inc. (Valencia, Calif.). User Guides that describe in great detail the protocol to be followed are usually included in all these kits. Sensitivity, processing time and cost may be different from one kit to another. One of ordinary skill in the art can easily select the kit(s) most appropriate for a particular situation.

Prior to extraction, cells containing *Neisseria gonorrhoeae* nucleic acids may be purified, concentrated or otherwise separated from other components of the original biological sample, for example, by filtration or centrifugation.

Sample Analysis

As will be appreciated by one skilled in the art, amplification of *Neisseria gonorrhoeae* target sequences and detection of amplified *Neisseria gonorrhoeae* nucleic acids according to inventive methods may be performed using any amplification/detection methodologies, such as those described herein.

In certain embodiments, detection of *Neisseria gonorrhoeae* in a test sample is performed using a TaqMan™ assay, and the formation of amplification products is monitored in a real time manner by fluorescence. In these embodiments, probes will be used that are labeled with a fluorescent reporter at the 5' end and a quencher moiety at the 3' end, as described herein. Optimization of amplification conditions and selection of amplification reaction reagents suitable for a TaqMan™ assay format are within the skill in the art.

In certain embodiments, an internal control or an internal standard is added to the biological sample (or to purified nucleic acids extracted from the biological sample) to serve as a control for extraction and/or target amplification. The internal control generally includes a sequence that differs from the target sequence(s) and is capable of amplification by the primers used to amplify the target *Neisseria gonorrhoeae* nucleic acid(s). The use of an internal control allows monitoring of the extraction process, amplification reaction, and detection, and control of the assay performance. The amplified control and amplified target are typically distinguished at the detection step by using different probes (e.g., labeled with different detectable agents) for the detection of the control and the target.

The presence of *Neisseria gonorrhoeae* in a test sample may be confirmed by repeating an assay according to the present invention using a different aliquot of the same biological test sample or using a different test sample (e.g., an endocervical swab if the first sample analyzed was a urine sample, or a urine sample collected at a different time). Confirmatory tests can also be performed by targeting a different region of the *Neisseria gonorrhoeae* chromosome using a different set of inventive primers. Alternatively or additionally, the presence of *Neisseria gonorrhoeae* in a test sample may be confirmed by performing a different assay (i.e., an assay based on a different methodology). For example, if the first analysis was performed using a TaqMan™ assay, a second analysis may be carried out using a transcription-mediated amplification (TMA) reaction.

Alternatively or additionally, the presence of *Neisseria gonorrhea* in a test sample may be confirmed by a different assay (e.g., isolation from cell culture).

III—Multiplex Assays for the Simultaneous Detection of *Neisseria gonorrhea* and Other Organisms As already mentioned, primer/probe sets of the present invention are specific for *Neisseria gonorrhoeae*. Accordingly, the present invention also provides methods for simultaneously detecting the presence of *Neisseria gonorrhoeae* and another organism in a test sample using a combination of at least two primer sets or primer/probe sets (i.e., one selected from the *Neisseria gonorrhoeae* specific sets disclosed herein and another selected from sets specific for the other organism to be tested).

Other organisms that can be detected simultaneously with *Neisseria gonorrhoeae* include, but are not limited to, any of the organisms listed in Table 4. In certain embodiments, the other organism to be tested simultaneously with *Neisseria gonorrhoeae* is *Chlamydia trachomatis*.

In particular, the present invention provides a method for the detection of *Neisseria gonorrhoeae* and/or *Chlamydia trachomatis* in a test sample, which comprises steps of: providing a test sample suspected of containing *Neisseria gonorrhoeae* nucleic acid and/or *Chlamydia trachomatis* nucleic acid; contacting the test sample with a primer/probe set disclosed herein under conditions to amplify all or part of the *Neisseria gonorrhoeae* nucleic acid, if present in the sample, to produce *Neisseria gonorrhoeae* amplicons; contacting the test sample with at least one primer/probe set specific for *Chlamydia trachomatis* under conditions to amplify all or part of the *Chlamydia trachomatis* nucleic acid, if present in the sample, to product *Chlamydia trachomatis* amplicons; and detecting any *Neisseria gonorrhoeae* amplicons and any *Chlamydia trachomatis* amplicons, wherein detection of *Neisseria gonorrhoeae* amplicons indicates the presence of *Neisseria gonorrhoeae* in the test sample, and wherein detection of *Chlamydia trachomatis* amplicons indicates the presence of *Chlamydia trachomatis* in the test sample.

In certain preferred embodiments, the primer/probe set specific for *Chlamydia trachomatis* is one described in International Application No. PCT/US2006/43394 (to Siemens Medical Solutions Diagnostics) (which is incorporated herein by reference in its entirety).

IV—Kits

In another aspect, the present invention provides kits comprising materials useful for the detection of gonococcal infection according to methods described herein. The inventive kits may be used by diagnostic laboratories, experimental laboratories, or practitioners.

Basic material and reagents required for the detection of *Neisseria gonorrhoeae* according to the present invention may be assembled together in a kit. In certain embodiments, kits comprise at least one inventive primer set or primer/probe set, and optionally, amplification reaction reagents. Each kit preferably comprises the reagents which render the procedure specific. Thus, a kit adapted for use with NASBA preferably contains primers with a RNA polymerase promoter linked to the target binding sequence, while a kit adapted for use with SDA preferably contains primers including a restriction endonuclease recognition site 5' to the target binding sequence. Similarly, when the kit is adapted for use in a 5' nuclease assay, such as the TaqMan™ assay, the detection probes preferably contain at least one fluorescent reporter moiety and at least one quencher moiety.

Suitable amplification reaction reagents include, for example, one or more of: buffers, reagents, enzymes having reverse transcriptase and/or polymerase activity or exonuclease activity, enzyme cofactors such as magnesium or manganese; salts; deoxynucleotide triphosphates (dNTPs) such as deoxyadenosine triphosphate (dATP), deoxyguanosine triphosphate (dGTP), deoxycytidine triphosphate (dCTP), deoxythymidine triphosphate (dTTP) and deoxyuridine triphosphate (dUTP) suitable for carrying out the amplification reaction. For example, a kit, adapted for use with NASBA, may contain suitable amounts of reverse transcriptase, RNase H and T7 RNA polymerase. In kits adapted for transcription amplification reactions, such as NASBA, buffers can be included that contain, for example, DMSO, which is known to enhance the amplification reaction.

Depending on the procedure, kits may further comprise one or more of: wash buffers and/or reagents, hybridization buffers and/or reagents, labeling buffers and/or reagents, and detection means. The buffers and/or reagents are preferably optimized for the particular amplification/detection technique for which the kit is intended. Protocols for using these buffers and reagents for performing different steps of the procedure may also be included in the kit.

Furthermore, kits may be provided with an internal control as a check on the amplification procedure and to prevent occurrence of false negative test results due to failures in the amplification procedure. An optimal control sequence is selected in such a way that it will not compete with the target nucleic acid sequence in the amplification reaction (as described above).

Kits may also contain reagents for the isolation of nucleic acids from biological specimens prior to amplification and/or for the purification or separation of *Neisseria gonorrhoeae* cells before nucleic acid extraction.

The reagents may be supplied in a solid (e.g., lyophilized) or liquid form. Kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the amplification/detection assay may also be provided. The individual containers are preferably maintained in close confinement for commercial sale.

Kits may also comprise instructions for using the amplification reaction reagents and primer sets or primer/probe described herein. Instructions for using kits according to one or more methods of the invention may comprise instructions for processing the biological sample, extracting nucleic acid molecules, and/or performing the test; instructions for interpreting the results obtained as well as a notice in the form prescribed by a governmental agency (e.g., FDA) regulating the manufacture, use or sale of pharmaceuticals or biological products.

EXAMPLES

The following example describes some of the preferred modes of making and practicing the present invention. However, it should be understood that this example is for illustrative purposes only and is not meant to limit the scope of the invention. Furthermore, unless the description in an Example is presented in the past tense, the text, like the rest of the specification, is not intended to suggest that experiments were actually performed or data were actually obtained.

Example 1

Specificity of *Chlamydia trachomatis/Neisseria gonorrhoeae* Multiplex Assay

A multiplex TaqMan kPCR assay was used to test fifteen (15) different *Chlamydia trachomatis* (CT) serovars (i.e., A, B, Ba, C, D, E, F, G, H, I, J, K, L1, L2 and L3) and forty-six (46) different *Neisseria gonorrhoeae* (GC) isolates.

The amplification and detection in a single, sealed reaction well were carried out using Stratagene's Mx3000P™ Real-Time PCR System (Stratagene Inc., San Diego, Calif.). The assay master mix used in these experiments contained Taq DNA Polymerase, buffer, reference dye (ROX), and $MgCl_2$, AmpErase UNG (1 units/µL), from Applied Biosystems (Perkin-Elmer Applied Biosystems, Foster City, Calif.) or QIAGEN (Hilden, Germany); TaqMan® oligonucleotide primers and probes of the invention were synthesized in-house or purchased from BioSearch Inc. The kPCR reaction mix was comprised of 25 µL of master mix and 25 µL of purified DNA.

The results obtained, which are reported in Table 4, show that the CT/GC multiplex assay can detect a broad rage of CT serovars and GC isolates.

The CT/GC multiplex PCR master mix was also challenged with 107 copies of genomic DNA from 74 closely related organisms (listed in Table 3), and showed no cross-reactivity.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. An isolated oligonucleotide comprising a nucleic acid sequence of about 15 to about 50 nucleotides which hybridizes to a portion of region 3949 to 4187 of the pivNG gene of *Neisseria gonorrhoeae*, wherein said isolated oligonucleotide is selected from the group consisting of SEQ ID NO: 19, SEQ ID NO: 20, SEQ ID NO: 35, SEQ ID NO: 36, SEQ ID NO: 38, SEQ ID NO: 41, SEQ ID NO: 48 and SEQ ID NO: 49.

2. The isolated oligonucleotide of claim 1 further comprising a detectable label.

3. The isolated oligonucleotide of claim 2, wherein the detectable label comprises a fluorescent moiety attached at the 5' end of the oligonucleotide.

4. The isolated oligonucleotide of claim 3, wherein said oligonucleotide further comprises a quencher moiety attached at its 3' end.

5. The isolated oligonucleotide of claim 4, wherein the fluorescent moiety comprises 6-carboxyfluorescein.

6. A collection of oligonucleotides for detecting *Neisseria gonorrhoeae* in a test sample, the collection comprising at least one oligonucleotide according to claim 1.

7. A collection of oligonucleotides according to claim 6 further comprising oligonucleotides comprising SEQ ID NO: 21, SEQ ID NO 34, or SEQ ID NO:46.

8. The collection of oligonucleotides of claim 7, wherein at least one of the oligonucleotides is a detection probe which comprises a detectable label.

9. The collection of oligonucleotides of claim 8, wherein the detectable label is directly attached to the at least one detection probe.

10. The collection of oligonucleotides of claim 8, wherein the detectable label is indirectly attached to the at least one detection probe.

11. The collection of oligonucleotides of claim 8, wherein the detectable label is directly detectable.

12. The collection of oligonucleotides of claim 8, wherein the detectable label is indirectly detectable.

13. The collection of oligonucleotides of claim 8, wherein the detectable label comprises a fluorescent moiety attached at the 5' end of the at least one detection probe.

14. The collection of oligonucleotides of claim 13, wherein the at least one detection probe further comprises a quencher moiety attached at its 3' end.

15. The collection of oligonucleotides of claim 14, wherein the fluorescent moiety comprises 6-carboxyfluroescein.

16. A kit for detecting *Neisseria gonorrhoeae* in a test sample comprising:
   amplification reaction reagents; and
   at least one primer according to claim 6.

17. A kit according to claim 16 further comprising at least one detection probe comprising SEQ ID NO: 21, SEQ ID NO 34, or SEQ ID NO:46.

18. The kit of claim 17, wherein at least one of the detection probes comprises a detectable label.

19. The kit of claim 18, wherein the detectable label is directly attached to the at least one detection probe.

20. The kit of claim 18, wherein the detectable label is indirectly attached to the at least one detection probe.

21. The kit of claim 18, wherein the detectable label is directly detectable.

22. The kit of claim 18, wherein the detectable label is indirectly detectable.

23. The kit of claim 18, wherein the detectable label comprises a fluorescent moiety attached at the 5' end of the at least one detection probe.

24. The kit of claim 23, wherein the at least one detection probe further comprises a quencher moiety attached at its 3' end.

25. The kit of claim 24, wherein the fluorescent moiety comprises 6-carboxyfluorescein.

26. A method for detecting *Neisseria gonorrhoeae* in a test sample, the method comprising steps of:
   providing a test sample suspected of containing a *Neisseria gonorrhoeae* nucleic acid;
   contacting the test sample with at least one isolated oligonucleotide according to claim 1 such that the at least one oligonucleotide hybridizes to the *Neisseria gonorrhoeae* nucleic acid, if present in the test sample; and
   detecting any oligonucleotide hybridized to the *Neisseria gonorrhoeae* nucleic acid, where detection of an oligonucleotide hybridized to the *Neisseria gonorrhoeae* nucleic acid indicates the presence of *Neisseria gonorrhoeae* in the test sample.

27. A method for detecting *Neisseria gonorrhoeae* in a test sample, the method comprising steps of:
   providing a test sample suspected of containing a *Neisseria gonorrhoeae* nucleic acid;
   contacting the test sample with a collection of oligonucleotides according to claim 7 under conditions such that all or part of the *Neisseria gonorrhoeae* nucleic acid is amplified, if present in the test sample, thereby generating *Neisseria gonorrhoeae* amplicons; and
   detecting any *Neisseria gonorrhoeae* amplicons, wherein detection of *Neisseria gonorrhoeae* amplicons indicates the presence of *Neisseria gonorrhoeae* in the test sample.

28. The method of claim 27 wherein contacting the test sample under conditions such that all or part of the *Neisseria gonorrhoeae* nucleic acid is amplified comprises submitting the test sample to a nucleic acid amplification reaction carried out under suitable amplification conditions and in the presence of suitable amplification reaction reagents.

29. The method of claim 26 wherein the test sample comprises a bodily fluid selected from the group consisting of urine, seminal fluid, saliva, ocular lens fluid, lymphatic fluid, endocervical, urethral, rectal, vaginal, vulva-vaginal, and nasopharyngeal samples.

* * * * *

SEQUENCE LISTING

<160> NUMBER OF SEQ ID NOS: 52

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide sequence

<400> SEQUENCE: 1
gcggattccc ttgtcaagat t                                    21

<210> SEQ ID NO 2
<211> LENGTH: 17
<212> TYPE: DNA
<213> ORGANISM: Artificial Sequence
<220> FEATURE:
<223> OTHER INFORMATION: Oligonucleotide sequenc

<400> SEQUENCE: 2
gccgcgctca ccctcta                                         17

<210> SEQ ID NO 3
<211> LENGTH: 24

```
<212> TYPE: DNA
<213> ORGANISM: Artificial Sequence
<220> FEATURE:
<223> OTHER INFORMATION: Oligonucleotide sequence

<400> SEQUENCE: 3
ttccatgatt tggaaacagc cggg                                              24

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide sequence

<400> SEQUENCE: 4
cccggctgtt tccaaatcat ggaa                                              24

<210> SEQ ID NO 5
<211> LENGTH: 27
<212> TYPE: DNA
<213> ORGANISM: Artificial Sequence
<220> FEATURE:
<223> OTHER INFORMATION: Oligonucleotide sequence

<400> SEQUENCE: 5
agtacgtttg gatacaggat ttgattt                                           27

<210> SEQ ID NO 6
<211> LENGTH: 19
<212> TYPE: DNA
<213> ORGANISM: Artificial Sequence
<220> FEATURE:
<223> OTHER INFORMATION: Oligonucleotide sequence

<400> SEQUENCE: 6
agccgttttc gccagtttc                                                    19

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide sequence

<400> SEQUENCE: 7
ccatccggaa ccgacgcaca a                                                 21

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide sequence

<400> SEQUENCE: 8
ggaacgagcc atcaaaaaca a                                                 21

<210> SEQ ID NO 9
<211> LENGTH: 21
<212> TYPE: DNA
<213> ORGANISM: Artificial Sequence
<220> FEATURE:
<223> OTHER INFORMATION: Oligonucleotide sequence

<400> SEQUENCE: 9
```
gcggttcagg gaagtgatag c                                               21

<210> SEQ ID NO 10
<211> LENGTH: 24
<212> TYPE: DNA
<213> ORGANISM: Artificial Sequence
<220> FEATURE:
<223> OTHER INFORMATION: Oligonucleotide sequence

<400> SEQUENCE: 10
ttgcagcagg tggcggtggt actt                                          24

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide sequence

<400> SEQUENCE: 11
aagtaccacc gccacctgct gcaa                                          24

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide sequence

<400> SEQUENCE: 12
aaggtatgat tagccacgtt tatcg                                         25

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide sequence

<400> SEQUENCE: 13
cgccacctgc tgcaataatt                                               20

<210> SEQ ID NO 14
<211> LENGTH: 26
<212> TYPE: DNA
<213> ORGANISM: Artificial Sequence
<220> FEATURE:
<223> OTHER INFORMATION: Oligonucleotide sequence

<400> SEQUENCE: 14
cgtatgcatc ggaacgagcc atcaaa                                        26

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide sequence

<400> SEQUENCE: 15 gcctttttc ctttcgggat t                                              21

<210> SEQ ID NO 16
<211> LENGTH: 25
<212> TYPE: DNA
<213> ORGANISM: Artificial Sequence -continued

```
<220> FEATURE:
<223> OTHER INFORMATION: Oligonucleotide sequence

<400> SEQUENCE: 16
gtacataaga aaggcggaga ttacg                                              25

<210> SEQ ID NO 17
<211> LENGTH: 23
<212> TYPE: DNA
<213> ORGANISM: Artificial Sequence
<220> FEATURE:
<223> OTHER INFORMATION: Oligonucleotide sequence

<400> SEQUENCE: 17
acgccgattt gtaacgcgat gga                                                23

<210> SEQ ID NO 18
<211> LENGTH: 23
<212> TYPE: DNA
<213> ORGANISM: Artificial Sequence
<220> FEATURE:
<223> OTHER INFORMATION: Oligonucleotide sequence

<400> SEQUENCE: 18
tccatcgcgt tacaaatcgg cgt                                                23

<210> SEQ ID NO 19
<211> LENGTH: 19
<212> TYPE: DNA
<213> ORGANISM: Artificial Sequence
<220> FEATURE:
<223> OTHER INFORMATION: Oligonucleotide sequence

<400> SEQUENCE: 19
gacgcttcac gccttcctt                                                     19

<210> SEQ ID NO 20
<211> LENGTH: 24
<212> TYPE: DNA
<213> ORGANISM: Artificial Sequence
<220> FEATURE:
<223> OTHER INFORMATION: Oligonucleotide sequence

<400> SEQUENCE: 20
ccatgaatga acagcttgaa gttt                                               24

<210> SEQ ID NO 21
<211> LENGTH: 33
<212> TYPE: DNA
<213> ORGANISM: Artificial Sequence
<220> FEATURE:
<223> OTHER INFORMATION: Oligonucleotide sequence

<400> SEQUENCE: 21
aggcttctcc gtctgctctt ttatcttctc ctt                                     33

<210> SEQ ID NO 22
<211> LENGTH: 22
<212> TYPE: DNA
<213> ORGANISM: Artificial Sequence
<220> FEATURE:
<223> OTHER INFORMATION: Oligonucleotide sequence

<400> SEQUENCE: 22
gcatcctgtt tgtctgtttt gg                                                 22
```

<210> SEQ ID NO 23
<211> LENGTH: 25
<212> TYPE: DNA
<213> ORGANISM: Artificial Sequence
<220> FEATURE:
<223> OTHER INFORMATION: Oligonucleotide sequence

<400> SEQUENCE: 23
ttacgtagtg aatccgctga aaata                          25

<210> SEQ ID NO 24
<211> LENGTH: 28
<212> TYPE: PRT
<213> ORGANISM: Artificial Sequence
<220> FEATURE:
<223> OTHER INFORMATION: Oligonucleotide sequence

<400> SEQUENCE: 24

Cys Gly Cys Thr Thr Gly Ala Ala Cys Cys Thr Gly Cys Thr Thr
1               5                   10                  15

Cys Thr Gly Cys Ala Thr Ala Cys Thr Thr Gly Cys
            20                  25

<210> SEQ ID NO 25
<211> LENGTH: 18
<212> TYPE: DNA
<213> ORGANISM: Artificial Sequence
<220> FEATURE:
<223> OTHER INFORMATION: Oligonucleotide sequence

<400> SEQUENCE: 25
ccgaatgctc cgttttgc                                  18

<210> SEQ ID NO 26
<211> LENGTH: 25
<212> TYPE: DNA
<213> ORGANISM: Artificial Sequence
<220> FEATURE:
<223> OTHER INFORMATION: Oligonucleotide sequence

<400> SEQUENCE: 26
gtaacgccgt aggattggat atatc                          25

<210> SEQ ID NO 27
<211> LENGTH: 25
<212> TYPE: DNA
<213> ORGANISM: Artificial Sequence
<220> FEATURE:
<223> OTHER INFORMATION: Oligonucleotide sequence

<400> SEQUENCE: 27
ccatggcgga tgcgttaaag gtcag                          25

<210> SEQ ID NO 28
<211> LENGTH: 25
<212> TYPE: DNA
<213> ORGANISM: Artificial Sequence
<220> FEATURE:
<223> OTHER INFORMATION: Oligonucleotide sequence

<400> SEQUENCE: 28 ctgacccttta acgcatccgc catgg                         25

<210> SEQ ID NO 29
<211> LENGTH: 26

```
<212> TYPE: DNA
<213> ORGANISM: Artificial Sequence
<220> FEATURE:
<223> OTHER INFORMATION: Oligonucleotide sequence

<400> SEQUENCE: 29
tgatctaaac cttttgaatc gttgtc                                          26

<210> SEQ ID NO 30
<211> LENGTH: 17
<212> TYPE: DNA
<213> ORGANISM: Artificial Sequence
<220> FEATURE:
<223> OTHER INFORMATION: Oligonucleotide sequence

<400> SEQUENCE: 30
aacgcatccg ccatggt                                                    17

<210> SEQ ID NO 31
<211> LENGTH: 25
<212> TYPE: DNA
<213> ORGANISM: Artificial Sequence
<220> FEATURE:
<223> OTHER INFORMATION: Oligonucleotide sequence

<400> SEQUENCE: 31
aactttgccg aatgctccgt tttgc                                           25

<210> SEQ ID NO 32
<211> LENGTH: 19
<212> TYPE: DNA
<213> ORGANISM: Artificial Sequence
<220> FEATURE:
<223> OTHER INFORMATION: Oligonucleotide sequence

<400> SEQUENCE: 32
gacgcttcac gccttcctt                                                  19

<210> SEQ ID NO 33
<211> LENGTH: 24
<212> TYPE: DNA
<213> ORGANISM: Artificial Sequence
<220> FEATURE:
<223> OTHER INFORMATION: Oligonucleotide sequence

<400> SEQUENCE: 33
ccatgaatga acagcttgaa gttt                                            24

<210> SEQ ID NO 34
<211> LENGTH: 19
<212> TYPE: DNA
<213> ORGANISM: Artificial Sequence
<220> FEATURE:
<223> OTHER INFORMATION: Oligonucleotide sequence

<400> SEQUENCE: 34
aggcttctcc gtctgctct                                                  19

<210> SEQ ID NO 35
<211> LENGTH: 21
<212> TYPE: DNA
<213> ORGANISM: Artificial Sequence
<220> FEATURE:
<223> OTHER INFORMATION: Oligonucleotide sequence

<400> SEQUENCE: 35
```

-continued

```
tctgcctatt gccggtatgg t                                              21

<210> SEQ ID NO 36
<211> LENGTH: 20
<212> TYPE: DNA
<213> ORGANISM: Artificial Sequence
<220> FEATURE:
<223> OTHER INFORMATION: Oligonucleotide sequence

<400> SEQUENCE: 36
gaagcggcca aagcatatgc                                                20

<210> SEQ ID NO 37
<211> LENGTH: 19
<212> TYPE: DNA
<213> ORGANISM: Artificial Sequence
<220> FEATURE:
<223> OTHER INFORMATION: Oligonucleotide sequence

<400> SEQUENCE: 37
aggcttctcc gtctgctct                                                 19

<210> SEQ ID NO 38
<211> LENGTH: 19
<212> TYPE: DNA
<213> ORGANISM: Artificial Sequence
<220> FEATURE:
<223> OTHER INFORMATION: Oligonucleotide sequence

<400> SEQUENCE: 38
attgccggta tggtttcaa                                                 19

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide sequence

<400> SEQUENCE: 39
gaagcggcca aagcatatgc                                                20

<210> SEQ ID NO 40
<211> LENGTH: 19
<212> TYPE: DNA
<213> ORGANISM: Artificial Sequence
<220> FEATURE:
<223> OTHER INFORMATION: Oligonucleotide sequence

<400> SEQUENCE: 40
aggcttctcc gtctgctct                                                 19

<210> SEQ ID NO 41
<211> LENGTH: 21
<212> TYPE: DNA
<213> ORGANISM: Artificial Sequence
<220> FEATURE:
<223> OTHER INFORMATION: Oligonucleotide sequence

<400> SEQUENCE: 41
gtcattctgc ctattgccgg t                                              21

<210> SEQ ID NO 42
<211> LENGTH: 20
<212> TYPE: DNA
<213> ORGANISM: Artificial Sequence
```

```
<220> FEATURE:
<223> OTHER INFORMATION: Oligonucleotide sequence

<400> SEQUENCE: 42
gaagcggcca aagcatatgc                                                 20

<210> SEQ ID NO 43
<211> LENGTH: 24
<212> TYPE: DNA
<213> ORGANISM: Artificial Sequence
<220> FEATURE:
<223> OTHER INFORMATION: Oligonucleotide sequence

<400> SEQUENCE: 43
tgcatccaat cagatttcct ttcg                                            24

<210> SEQ ID NO 44
<211> LENGTH: 21
<212> TYPE: DNA
<213> ORGANISM: Artificial Sequence
<220> FEATURE:
<223> OTHER INFORMATION: Oligonucleotide sequence

<400> SEQUENCE: 44
tctgcctatt gccggtatgg t                                               21

<210> SEQ ID NO 45
<211> LENGTH: 20
<212> TYPE: DNA
<213> ORGANISM: Artificial Sequence
<220> FEATURE:
<223> OTHER INFORMATION: Oligonucleotide sequence

<400> SEQUENCE: 45
gaagcggcca aagcatatgc                                                 20

<210> SEQ ID NO 46
<211> LENGTH: 23
<212> TYPE: DNA
<213> ORGANISM: Artificial Sequence
<220> FEATURE:
<223> OTHER INFORMATION: Oligonucleotide sequence

<400> SEQUENCE: 46
gcttcacgcc ttccttgcag tta                                             23

<210> SEQ ID NO 47
<211> LENGTH: 21
<212> TYPE: DNA
<213> ORGANISM: Artificial Sequence
<220> FEATURE:
<223> OTHER INFORMATION: Oligonucleotide sequence

<400> SEQUENCE: 47
tctgcctatt gccggtatgg t                                               21

<210> SEQ ID NO 48
<211> LENGTH: 20
<212> TYPE: DNA
<213> ORGANISM: Artificial Sequence
<220> FEATURE:
<223> OTHER INFORMATION: Oligonucleotide sequence

<400> SEQUENCE: 48
gaagcggcca aagcatatgc                                                 20
```

```
<210> SEQ ID NO 49
<211> LENGTH: 20
<212> TYPE: DNA
<213> ORGANISM: Artificial Sequence
<220> FEATURE:
<223> OTHER INFORMATION: Oligonucleotide sequence

<400> SEQUENCE: 49
tcacgccttc cttgcagtta                                              20

<210> SEQ ID NO 50
<211> LENGTH: 26
<212> TYPE: DNA
<213> ORGANISM: Artificial Sequence
<220> FEATURE:
<223> OTHER INFORMATION: Oligonucleotide sequence

<400> SEQUENCE: 50
tgatctaaac cttttgaatc gttgtc                                       26

<210> SEQ ID NO 51
<211> LENGTH: 25
<212> TYPE: DNA
<213> ORGANISM: Artificial Sequence
<220> FEATURE:
<223> OTHER INFORMATION: Oligonucleotide sequence

<400> SEQUENCE: 51
gtaacgccgt aggattggat atatc                                        25

<210> SEQ ID NO 52
<211> LENGTH: 25
<212> TYPE: DNA
<213> ORGANISM: Artificial Sequence
<220> FEATURE:
<223> OTHER INFORMATION: Oligonucleotide sequence

<400> SEQUENCE: 52
ccatggcgga tgcgttaaag gtcag                                        25
```